US012564462B2

(12) United States Patent
Ueda et al.

(10) Patent No.: US 12,564,462 B2
(45) Date of Patent: Mar. 3, 2026

(54) ROBOTIC SURGICAL SYSTEM AND OPERATOR-SIDE APPARATUS

(71) Applicant: KAWASAKI JUKOGYO KABUSHIKI KAISHA, Kobe (JP)

(72) Inventors: Tatsuya Ueda, Kobe (JP); Kazuya Momma, Kobe (JP); Hiroki Shibata, Kobe (JP); Hirotaka Kuno, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 201 days.

(21) Appl. No.: 18/574,773

(22) PCT Filed: Jun. 29, 2022

(86) PCT No.: PCT/JP2022/025975
§ 371 (c)(1),
(2) Date: Dec. 28, 2023

(87) PCT Pub. No.: WO2023/277066
PCT Pub. Date: Jan. 5, 2023

(65) Prior Publication Data
US 2024/0325101 A1 Oct. 3, 2024

(30) Foreign Application Priority Data

Jun. 30, 2021 (JP) ................................. 2021-109575
Nov. 15, 2021 (JP) ................................. 2021-185942

(51) Int. Cl.
*A61B 34/37* (2016.01)
*A61B 1/00* (2006.01)
(Continued)

(52) U.S. Cl.
CPC ............ *A61B 34/37* (2016.02); *A61B 1/0004* (2022.02); *A61B 1/0005* (2013.01);
(Continued)

(58) Field of Classification Search
CPC ....... A61B 34/37; A61B 34/74; A61B 1/0004; A61B 1/0005; A61B 1/00188; A61B 1/043
See application file for complete search history.

(56) References Cited

U.S. PATENT DOCUMENTS

| | | | | |
|---|---|---|---|---|
| 6,246,200 B1 * | 6/2001 | Blumenkranz | ........ | A61B 34/70 |
| | | | | 318/568.25 |
| 8,638,057 B2 | 1/2014 | Goldberg et al. | | |

(Continued)

FOREIGN PATENT DOCUMENTS

| | | |
|---|---|---|
| EP | 3245975 A1 | 11/2017 |
| JP | S61-93520 A | 5/1986 |

(Continued)

*Primary Examiner* — Aaron B Fairchild
(74) *Attorney, Agent, or Firm* — METROLEX IP LAW GROUP, PLLC; Robert L. Scott, Esq.

(57) ABSTRACT

An operator-side apparatus includes an operation manipulator including an operation unit to receive an operation for a surgical instrument, the operation manipulator being operable to move a robot arm. The operation unit includes a customized switch in which a function to be performed by the customized switch is customized by function setting by an operator.

20 Claims, 16 Drawing Sheets

(51) Int. Cl.

| | |
|---|---|
| *A61B 1/04* | (2006.01) |
| *A61B 34/00* | (2016.01) |
| *B25J 13/02* | (2006.01) |
| *A61B 34/30* | (2016.01) |

(52) U.S. Cl.
CPC .......... *A61B 1/00188* (2013.01); *A61B 1/043* (2013.01); *A61B 34/74* (2016.02); *B25J 13/02* (2013.01); *A61B 2034/301* (2016.02)

(56) References Cited

U.S. PATENT DOCUMENTS

| | | | |
|---|---|---|---|
| 2003/0109857 A1 | 6/2003 | Sanchez et al. | |
| 2005/0043719 A1 | 2/2005 | Sanchez et al. | |
| 2009/0245600 A1 | 10/2009 | Hoffman et al. | |
| 2010/0225209 A1 | 9/2010 | Goldberg et al. | |
| 2011/0037876 A1* | 2/2011 | Talbert ............... | A61B 1/00055 |
| | | | 348/222.1 |
| 2011/0301616 A1 | 12/2011 | Sanchez et al. | |
| 2017/0071681 A1 | 3/2017 | Peine | |
| 2020/0275985 A1 | 9/2020 | Thompson et al. | |
| 2020/0375673 A1 | 12/2020 | Peine | |
| 2020/0390510 A1 | 12/2020 | Thompson et al. | |
| 2021/0030257 A1 | 2/2021 | Ishihara | |
| 2021/0330409 A1 | 10/2021 | Kitatsuji et al. | |
| 2022/0175478 A1 | 6/2022 | Kawabata et al. | |
| 2022/0221982 A1 | 7/2022 | Hayamizu et al. | |

FOREIGN PATENT DOCUMENTS

| | | | |
|---|---|---|---|
| JP | S63-84116 | U | 6/1988 |
| JP | H02-14736 | U | 1/1990 |
| JP | H06-46043 | Y2 | 11/1994 |
| JP | 2005-511334 | A | 4/2005 |
| JP | 2009-213540 | A | 9/2009 |
| JP | 2009-226170 | A | 10/2009 |
| JP | 2012-65698 | A | 4/2012 |
| JP | 2016-087253 | A | 5/2016 |
| JP | 2017-99820 | A | 6/2017 |
| JP | 2017-525401 | A | 9/2017 |
| JP | 2021-19949 | A | 2/2021 |
| JP | 2021-171457 | A | 11/2021 |
| JP | 2022-88805 | A | 6/2022 |
| WO | 2020/230851 | A1 | 11/2020 |

* cited by examiner

FIRST GRAPHICAL DISPLAY GR1

SECOND GRAPHICAL DISPLAY GR2

ROBOTIC SURGICAL SYSTEM AND OPERATOR-SIDE APPARATUS

TECHNICAL FIELD

The present disclosure relates to a robotic surgical system and an operator-side apparatus, and more particularly, it relates to a robotic surgical system and an operator-side apparatus, each of which operates a patient-side apparatus including a robot arm having a tip end to which a surgical instrument is attached.

BACKGROUND ART

Conventionally, an operator-side apparatus that operates a patient-side apparatus including a robot arm having a tip end to which a surgical instrument is attached is known.

For example, U.S. Pat. No. 8,638,057 discloses a console that operates a robotic surgical manipulator including a robot arm having a tip end to which a surgical tool is attached. The console includes a master grip that is operated by the fingers of an operator such as a surgeon. The master grip is used to generate control signals to control the surgical tool. The master grip includes a tubular support structure, and a first grip and a second grip each having one end supported by the tubular support structure. A slidable switch that can be operated by the fingers of the operator is attached to the tubular support structure. The switch is described as performing a clutch function. U.S. Pat. No. 8,638,057 also describes that the switch performs, in addition to the clutch function, a multi-dimensional computer mouse function, an energy device activation function, or an arm swap function.

PRIOR ART

Patent Document

Patent Document 1: U.S. Pat. No. 8,638,057

SUMMARY OF THE INVENTION

In U.S. Pat. No. 8,638,057, the executable functions of the switch are predetermined and cannot be changed freely by the operator. Therefore, it is desired to increase the degree of freedom in the function performed by the switch.

The present disclosure is intended to solve the above problem. The present disclosure aims to provide a robotic surgical system and an operator-side apparatus each capable of increasing the degree of freedom in a function performed by a switch arranged on an operation unit.

In order to attain the aforementioned object, a robotic surgical system according to a first aspect of the present disclosure includes a patient-side apparatus including a robot arm having a tip end to which a surgical instrument is attached, and an operator-side apparatus including an operation manipulator including an operation unit to receive an operation for the surgical instrument, the operation manipulator being operable to move the robot arm. The operation unit includes a customized switch in which a function to be performed by the customized switch is customized by function setting by an operator.

In the robotic surgical system according to the first aspect of the present disclosure, as described above, the operation unit includes the customized switch in which a function to be performed by the customized switch is customized by function setting by the operator. Accordingly, the operator can set a function desired by the operator as a function to be performed by the customized switch, and thus the function to be performed by the customized switch can be changed. Consequently, the degree of freedom in the function performed by the customized switch arranged on the operation unit can be increased.

An operator-side apparatus according to a second aspect of the present disclosure is operable to move a robot arm having a tip end to which a surgical instrument is attached, and includes an operation manipulator including an operation unit to receive an operation for the surgical instrument. The operation unit includes a customized switch in which a function to be performed by the customized switch is customized by function setting by an operator.

In the operator-side apparatus according to the second aspect of the present disclosure, as described above, the operation unit includes the customized switch in which a function to be performed by the customized switch is customized by function setting by the operator. Accordingly, the operator can set a function desired by the operator as a function to be performed by the customized switch, and thus the function to be performed by the customized switch can be changed. Consequently, it is possible to provide the operator-side apparatus capable of increasing the degree of freedom in the function performed by the customized switch arranged on the operation unit.

According to the present disclosure, it is possible to increase the degree of freedom in the function performed by the switch arranged on the operation unit.

MODES FOR CARRYING OUT THE INVENTION

An embodiment embodying the present disclosure is hereinafter described on the basis of the drawings.

Present Embodiment

The configuration of a surgical system 100 according to the present embodiment is now described with reference to FIGS. 1 to 21.

Figure 1:
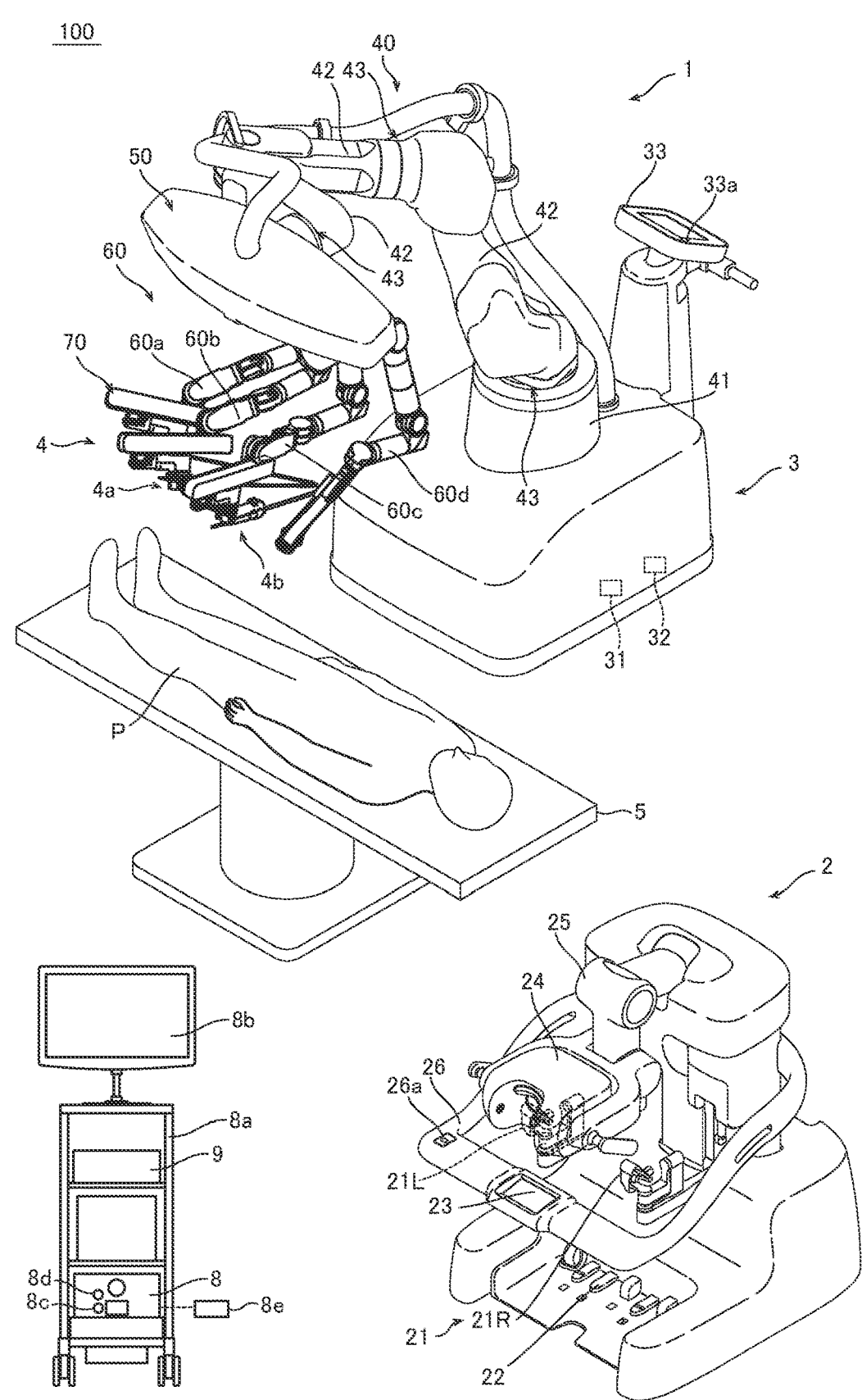
FIG. 1 is a diagram showing the configuration of a surgical system according to the present embodiment.

As shown in FIG. 1, the surgical system 100 includes a medical manipulator 1 that is a patient-side apparatus, a remote control apparatus 2 that is an operator-side apparatus to operate the medical manipulator 1, a controller 8, and an image processing unit 9. The medical manipulator 1 includes a medical cart 3 and is movable. The remote control apparatus 2 is spaced apart from the medical manipulator 1, and the medical manipulator 1 is remotely operated by the remote control apparatus 2. A surgeon inputs a command to the remote control apparatus 2 to cause the medical manipulator 1 to perform a desired operation. The remote control apparatus 2 transmits the input command to the medical manipulator 1. The medical manipulator 1 operates based on the received command. The medical manipulator 1 is arranged in an operating room that is a sterilized sterile field. The surgical system 100 is an example of a robotic surgical system. The medical manipulator 1 and the remote control apparatus 2 are examples of a patient-side apparatus and an operator-side apparatus, respectively.

The remote control apparatus 2 is arranged inside or outside the operating room, for example. The remote control apparatus 2 includes an operation manipulator 21, operation pedals 22, a touch panel 23, a monitor 24, a support arm 25, a support bar 26, and an error reset button 26a. The operation manipulator 21 includes operation handles for the surgeon to input commands. The operation manipulator 21 receives the amount of operation for a surgical instrument 4. The monitor 24 is a scope-type display that displays an image GR21 captured by an endoscope 4b. The support arm 25 supports the monitor 24 so as to align the height of the monitor 24 with the height of the face of the surgeon. The touch panel 23 is arranged on the support bar 26. The head of the surgeon is detected by a sensor provided in the vicinity of the monitor 24 such that the medical manipulator 1 can be operated by the remote control apparatus 2. The surgeon operates the operation manipulator 21 and the operation pedals 22 while visually recognizing an affected area on the monitor 24. Thus, a command is input to the remote control apparatus 2. The command input to the remote control apparatus 2 is transmitted to the medical manipulator 1. The operation manipulator 21 includes a right-hand operation manipulator 21R and a left-hand operation manipulator 21L. The error reset button 26a is arranged on the support bar 26. The error reset button 26a cancels errors in the surgical system 100. The surgical instrument 4 is an example of a first surgical instrument or a second surgical instrument. The operation manipulator 21 is an example of an operation arm. The touch panel 23 is an example of a function setting display. The monitor 24 is an example of a first display.

The controller 8 and the image processing unit 9 are placed on a cart 8a. The image processing unit 9 processes the image GR21 captured by the endoscope 4b. A display 8b is arranged on the cart 8a. In the present embodiment, the display 8b is arranged independently of the medical manipulator 1 and the remote control apparatus 2. The image GR21 captured by the endoscope 4b is displayed on the display 8b. An error reset button 8c and a notifier 8d are arranged on the controller 8. The error reset button 8c cancels errors in the surgical system 100. The display 8b is an example of a second display.

Figure 2:
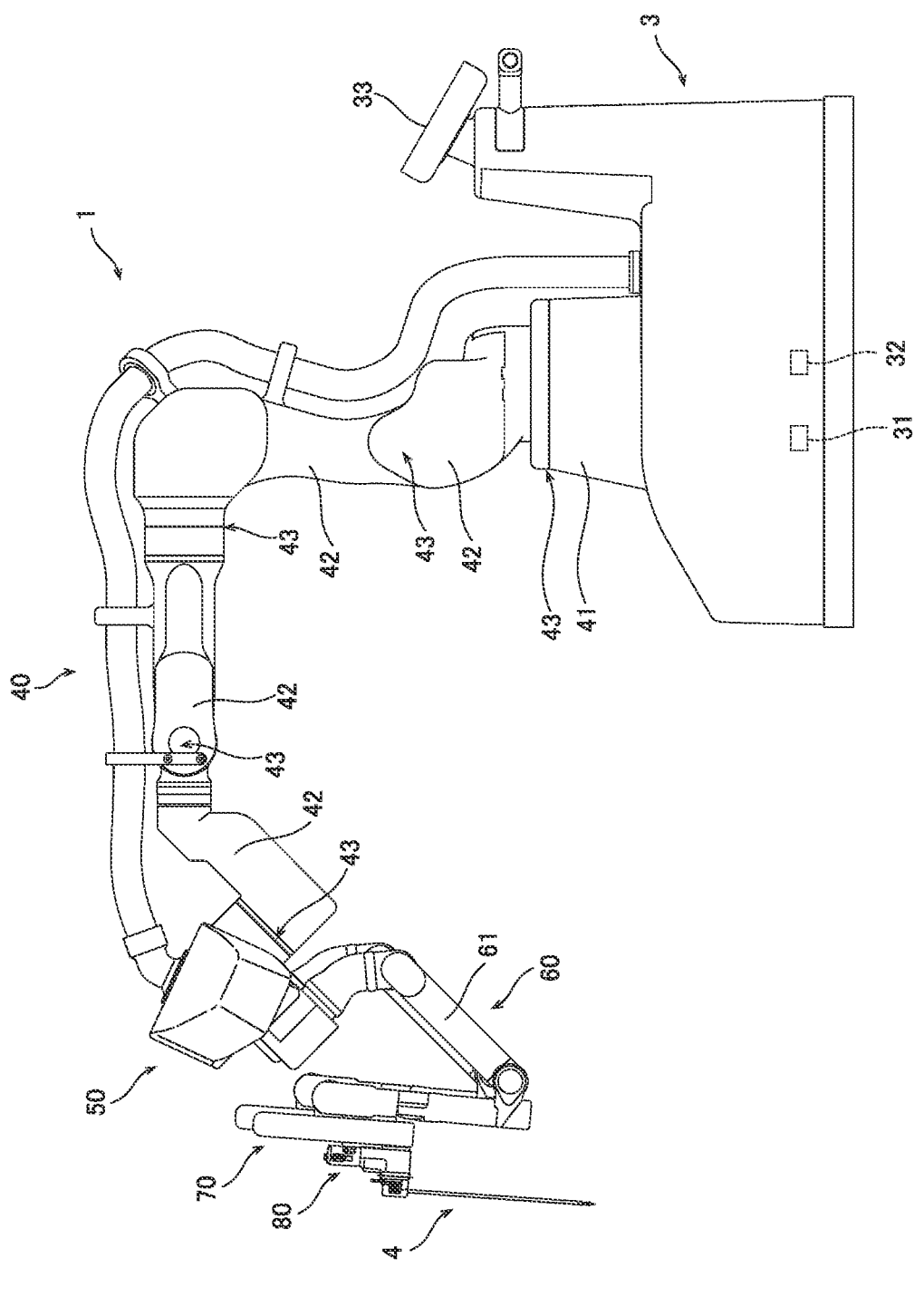
FIG. 2 is a diagram showing the configuration of a patient-side apparatus according to the present embodiment.

As shown in FIGS. 1 and 2, the medical cart 3 includes a controller 31 that controls the operation of the medical manipulator 1 and a storage 32 that stores programs or the like to control the operation of the medical manipulator 1. The controller 31 of the medical cart 3 controls the operation of the medical manipulator 1 based on the command input to the remote control apparatus 2.

The medical cart 3 includes an input 33. The input 33 receives operations to move a positioner 40, an arm base 50, and a plurality of manipulator arms 60 or change their postures mainly in order to prepare for surgery before the surgery. An error reset button 33a is arranged on the input 33. The error reset button 33a cancels errors in the surgical system 100.

The medical manipulator 1 shown in FIGS. 1 and 2 is arranged in the operating room. The medical manipulator 1 includes the medical cart 3, the positioner 40, the arm base 50, and the plurality of manipulator arms 60. The arm base 50 is attached to the tip end of the positioner 40. The arm base 50 has a relatively long rod shape. The bases of the plurality of manipulator arms 60 are attached to the arm base 50. Each of the plurality of manipulator arms 60 is able to take a folded and stored posture. The arm base 50 and the plurality of manipulator arms 60 are covered with sterile drapes and used.

The positioner 40 includes a 7-axis articulated robot, for example. The positioner 40 is arranged on the medical cart 3. The positioner 40 moves the arm base 50. Specifically, the positioner 40 moves the position of the arm base 50 three-dimensionally.

The positioner 40 includes a base 41 and a plurality of links 42 coupled to the base 41. The plurality of links 42 are coupled to each other by joints 43.

Surgical instruments 4 are attached to the tip ends of the plurality of manipulator arms 60. The surgical instruments 4 include a replaceable instrument 4a and the endoscope 4b, for example. The manipulator arms 60 are examples of a robot arm.

The configuration of the manipulator arms 60 is now described in detail with reference to FIG. 3.

Figure 3:
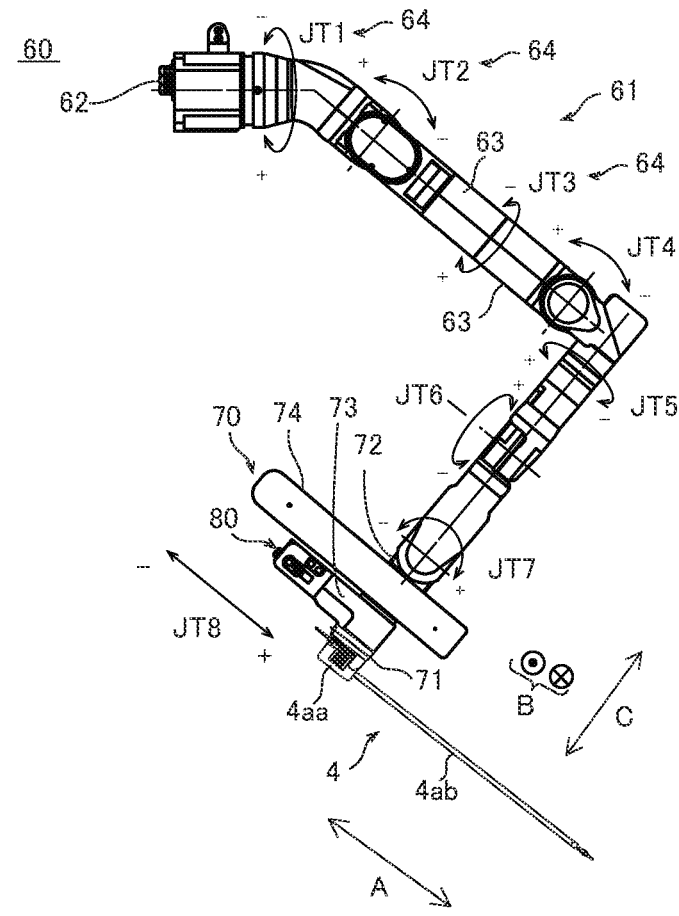
FIG. 3 is a diagram showing the configuration of a robot arm of the patient-side apparatus according to the present embodiment.

As shown in FIG. 3, each of the manipulator arms 60 includes an arm portion 61 and a translation mechanism 70 provided at the tip end of the arm portion 61. The tip end side of the manipulator arm 60 three-dimensionally moves with respect to the arm base 50 on the base side of the manipulator arm 60. The manipulator arm 60 has eight degrees of freedom. Specifically, the manipulator arm 60 includes JT1 to JT7 axes as rotation axes and a JT8 axis as a linear motion axis. The plurality of manipulator arms 60 have the same or similar configurations as each other. The arm portion 61 includes a base 62, links 63, and joints 64.

The translation mechanism 70 is provided at the tip end of the arm portion 61, and the surgical instrument 4 is attached thereto. The translation mechanism 70 translates the surgical instrument 4 in a direction in which the surgical instrument 4 is inserted into a patient P placed on a surgical table 5. Furthermore, the translation mechanism 70 translates the surgical instrument 4 relative to the arm portion 61. Specifically, the translation mechanism 70 includes a holder 71 that holds the surgical instrument 4. Servomotors are housed in the holder 71. The servomotors rotate rotary bodies provided in a driven unit 4*aa* of the surgical instrument 4. The rotary bodies of the driven unit 4*aa* are rotated such that the surgical instrument 4 operates.

The arm portion 61 includes a 7-axis articulated robot arm. The arm portion 61 includes the base 62 to attach the arm portion 61 to the arm base 50, and a plurality of links 63 coupled to the base 62. The plurality of links 63 are coupled to each other by the joints 64.

The translation mechanism 70 translates the surgical instrument 4 attached to the holder 71 along an A direction in which a shaft 4*ab* extends by translating the holder 71 along the A direction. Specifically, the translation mechanism 70 includes a base end side link 72 connected to the tip end of the arm portion 61, a tip end side link 73, and a coupling link 74 provided between the base end side link 72 and the tip end side link 73. The holder 71 is provided on the tip end side link 73.

The coupling link 74 of the translation mechanism 70 is configured as a double speed mechanism that moves the tip end side link 73 relative to the base end side link 72 along the A direction. The tip end side link 73 is moved along the A direction relative to the base end side link 72 such that the surgical instrument 4 attached to the holder 71 is translated along the A direction. The tip end of the arm portion 61 is connected to the base end side link 72 so as to rotate the base end side link 72 about a B direction orthogonal to the A direction.

As shown in FIG. 1, the endoscope 4*b* is attached to one of the plurality of manipulator arms 60, such as a manipulator arm 60*c*, and instruments 4*a* that are surgical instruments 4 other than the endoscope 4*b* are attached to the remaining manipulator arms 60*a*, 60*b*, and 60*d*. A pivot position PP is taught with the endoscope 4*b* attached to the manipulator arm 60 to which the endoscope 4*b* is to be attached. Furthermore, pivot positions PP are taught with pivot position teaching instruments attached to the manipulator arms 60 to which the instruments 4*a* other than the endoscope 4*b* are to be attached. The endoscope 4*b* is attached to one of two manipulator arms 60*b* and 60*c* arranged in the center among four manipulator arms 60 arranged adjacent to each other. That is, the pivot position PP is individually set for each of the plurality of manipulator arms 60. The manipulator arms 60*a*, 60*b*, and 60*d* are examples of a first surgical instrument robot arm or a second surgical instrument robot arm. The manipulator arm 60*c* is an example of an endoscope robot arm.

As shown in FIG. 3, an arm operation unit 80 is attached to the manipulator arm 60. Specifically, the arm operation unit 80 is attached to the tip end side link 73.

Figure 4:
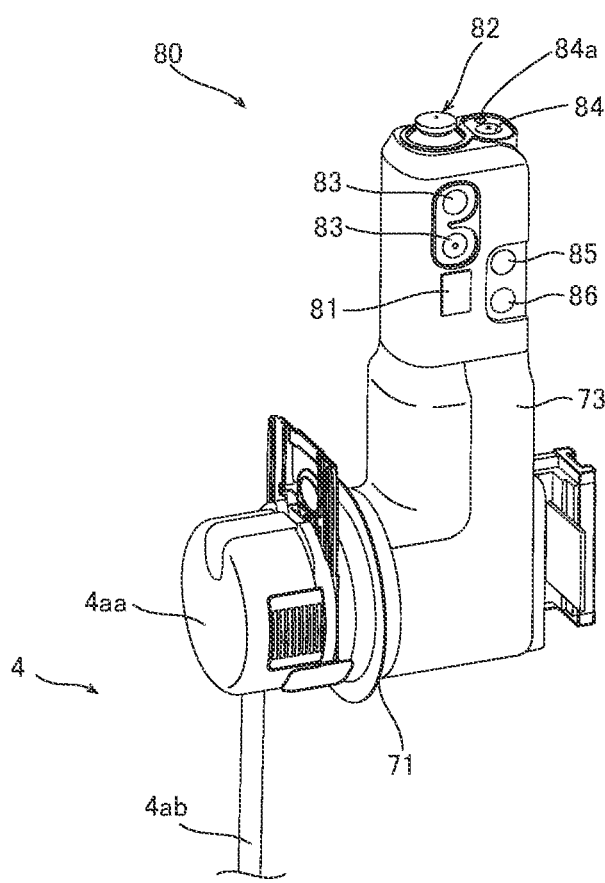
FIG. 4 is a perspective view showing the configuration of an arm operation unit according to the present embodiment.

As shown in FIG. 4, the arm operation unit 80 includes an enable switch 81, a joystick 82, linear switches 83, a mode switching button 84, a mode indicator 84*a*, a pivot button 85, and an adjustment button 86.

The enable switch 81 is a switch for enabling or disabling movement of the manipulator arm 60 in response to the joystick 82 and the linear switches 83. The joystick 82 is an operational tool for operating movement of the surgical instrument 4 by the manipulator arm 60. The linear switches 83 are switches for moving the surgical instrument 4 in a direction along the longitudinal direction of the surgical instrument 4. The mode switching button 84 is a button for switching between a mode for translating the surgical instrument 4 and a mode for rotationally moving the surgical instrument 4. The mode indicator 84*a* indicates a switched mode. The pivot button 85 is a button for teaching the pivot position PP that serves as a fulcrum for movement of the surgical instrument 4 attached to the manipulator arm 60. The adjustment button 86 is a button for optimizing the position of the manipulator arm 60.

The configuration of the operation manipulator 21 is now described in detail.

Figure 5:
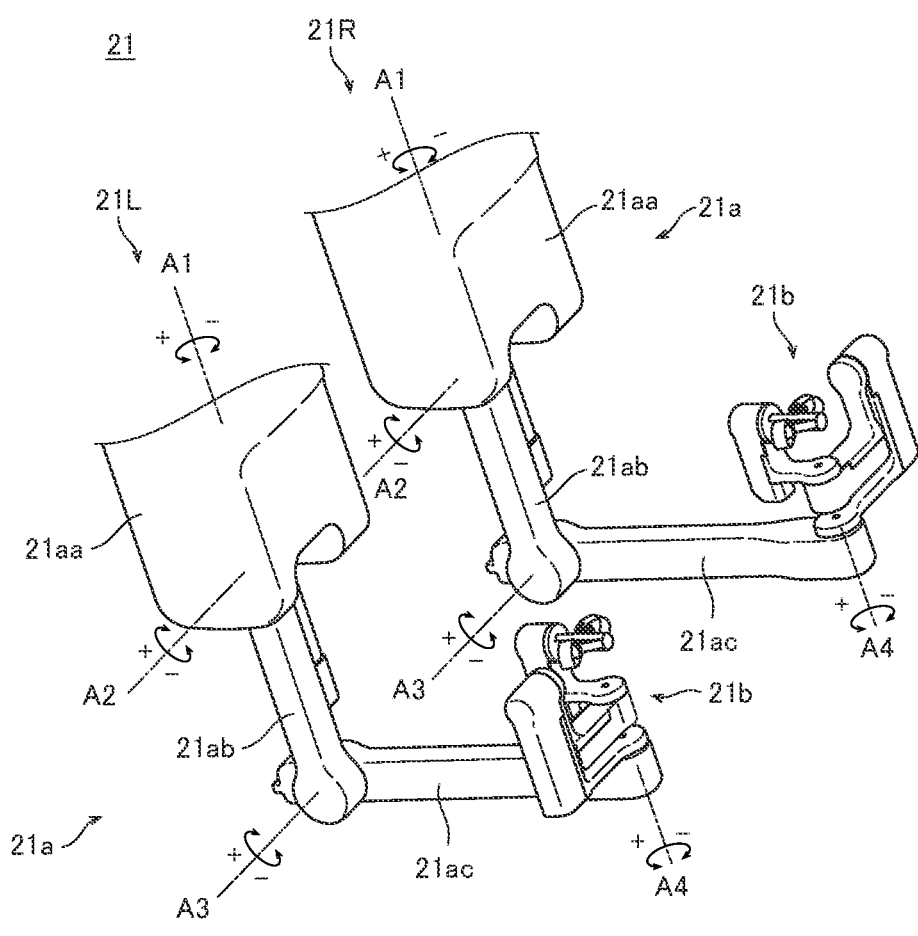
FIG. 5 is a perspective view showing the configuration of an operation arm of a remote control apparatus according to the present embodiment.

As shown in FIG. 5, the operation manipulator 21 includes the operation manipulator 21L located on the left side as viewed from an operator such as a surgeon and operated by the left hand of the operator, and the operation manipulator 21R located on the right side and operated by the right hand of the operator. The configurations of the operation manipulator 21L and the operation manipulator 21R are the same as or similar to each other except that operation units 21*b* thereof have bilaterally symmetrical structures.

The operation manipulator 21 includes operation arms 21*a* and the operation units 21*b*. Each of the operation arms 21*a* includes a link 21*aa*, a link 21*ab*, and a link 21*ac*. The upper end side of the link 21*aa* is attached to a main body of the remote control apparatus 2 such that the link 21*aa* is rotatable about an A1 axis along a vertical direction. The upper end side of the link 21*ab* is attached to the lower end side of the link 21*aa* such that the link 21*ab* is rotatable about an A2 axis along a horizontal direction. A first end side of the link 21*ac* is attached to the lower end side of the link 21*ab* such that the link 21*ac* is rotatable about an A3 axis along the horizontal direction.

The operation arms 21*a* support the operation units 21*b* such that the operation units 21*b* are movable within predetermined three-dimensional operation ranges. Specifically, the operation arms 21*a* support the operation units 21*b* such that the operation units 21*b* are movable in an upward-downward direction, a right-left direction, and a forward-rearward direction. The manipulator arms 60 are moved three-dimensionally so as to correspond to the three-dimensional operations of the operation arms 21*a*.

Figure 6:
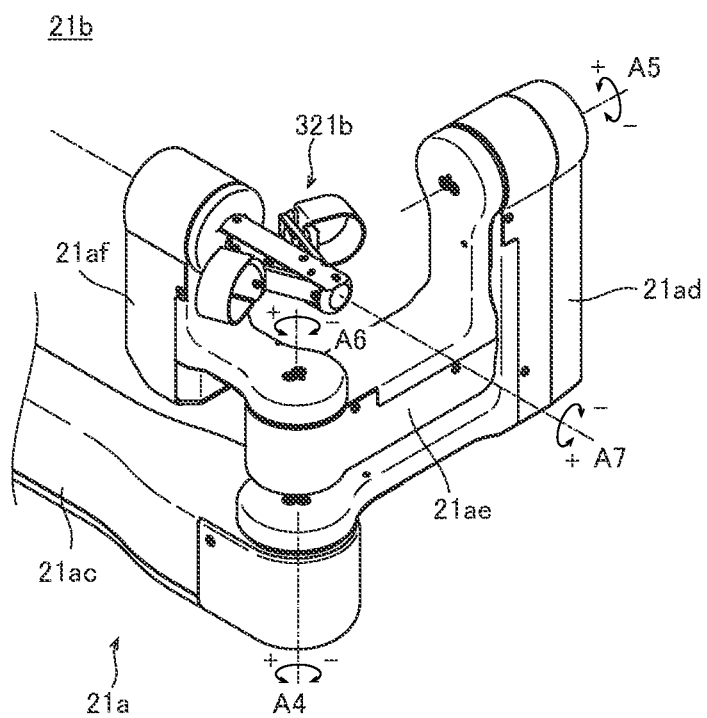
FIG. 6 is a perspective view showing the configuration of the operation arm and an operation handle according to the present embodiment.

As shown in FIG. 6, the operation unit 21*b* of the right-hand operation manipulator 21R includes a link 21*ad*, a link 21*ae*, a link 21*af*, and an operation handle 321*b*. A first end side of the link 21*ad* is attached to a second end side of the link 21*ac* such that the link 21*ad* is rotatable about an A4 axis. A first end side of the link 21*ae* is attached to a second end side of the link 21*ad* such that the link 21*ae* is rotatable about an A5 axis. A first end side of the link 21*af* is attached to a second end side of the link 21*ae* such that the link 21*af* is rotatable about an A6 axis.

Figure 7:
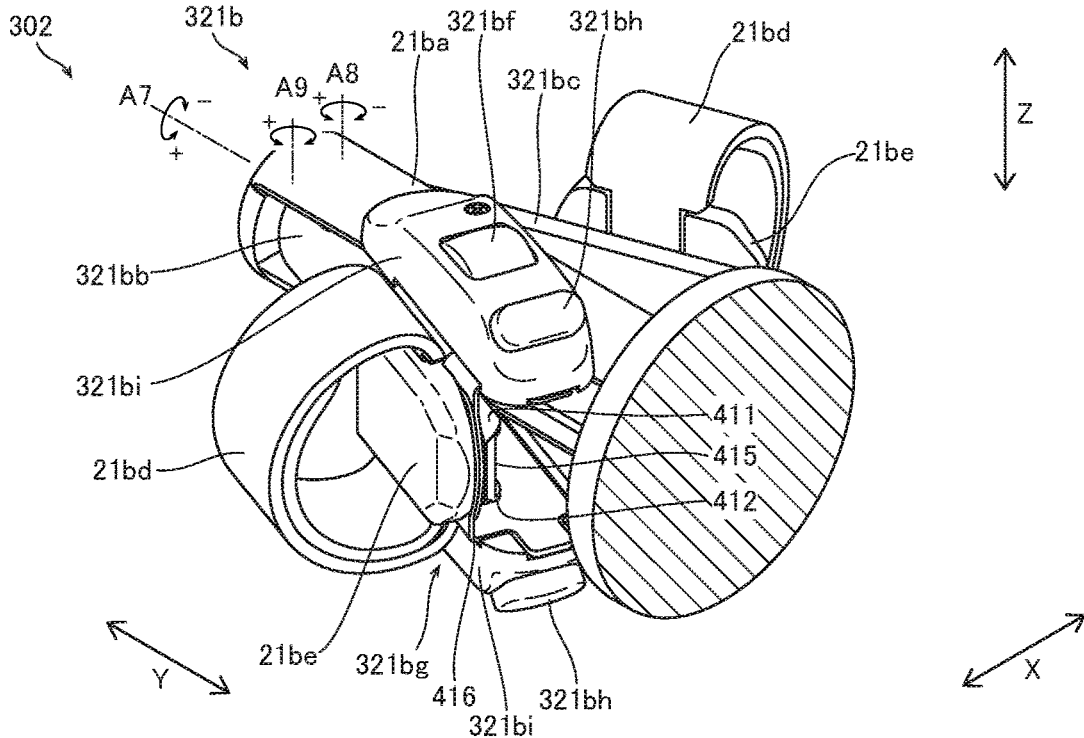
FIG. 7 is a perspective view (1) showing the configuration of the operation handle according to the present embodiment.

As shown in FIG. 7, the operation handle 321*b* includes a support member 21*ba*, a first lever member 321*bb*, and a second lever member 321*bc*. The first lever member 321*bb* is an example of a lever member.

The first lever member 321bb has an elongated plate shape, and is attached to the support member 21ba so as to rotate with respect to the support member 21ba. The first lever member 321bb is attached to the support member 21ba so as to rotate about an A9 axis perpendicular to an A7 axis with respect to the support member 21ba. The first lever member 321bb faces the second lever member 321bc via the support member 21ba.

The second lever member 321bc has an elongated plate shape, and is attached to the support member 21ba so as to rotate with respect to the support member 21ba. The second lever member 321bc is attached to the support member 21ba so as to rotate about an A8 axis perpendicular to the A7 axis with respect to the support member 21ba. The second lever member 321bc faces the first lever member 321bb via the support member 21ba.

A finger insertion portion 21bd and a finger pad 21be are arranged on each of the first lever member 321bb and the second lever member 321bc.

The operation handle 321b further includes a first switch 321bf attached to the first lever member 321bb to perform a predetermined function. The first switch 321bf is a clutch switch that performs a clutch function of preventing an operation of the operator from being transmitted to the medical manipulator 1. For example, when the operator operates the first lever member 321bb with the middle finger of the right hand and operates the second lever member 321bc with the thumb of the right hand, the operator closes the first lever member 321bb and the second lever member 321bc (a state shown in FIG. 8) and operates the first switch 321bf with the index finger of the right hand that is not operating the first lever member 321bb or the second lever member 321bc.

Figure 8:
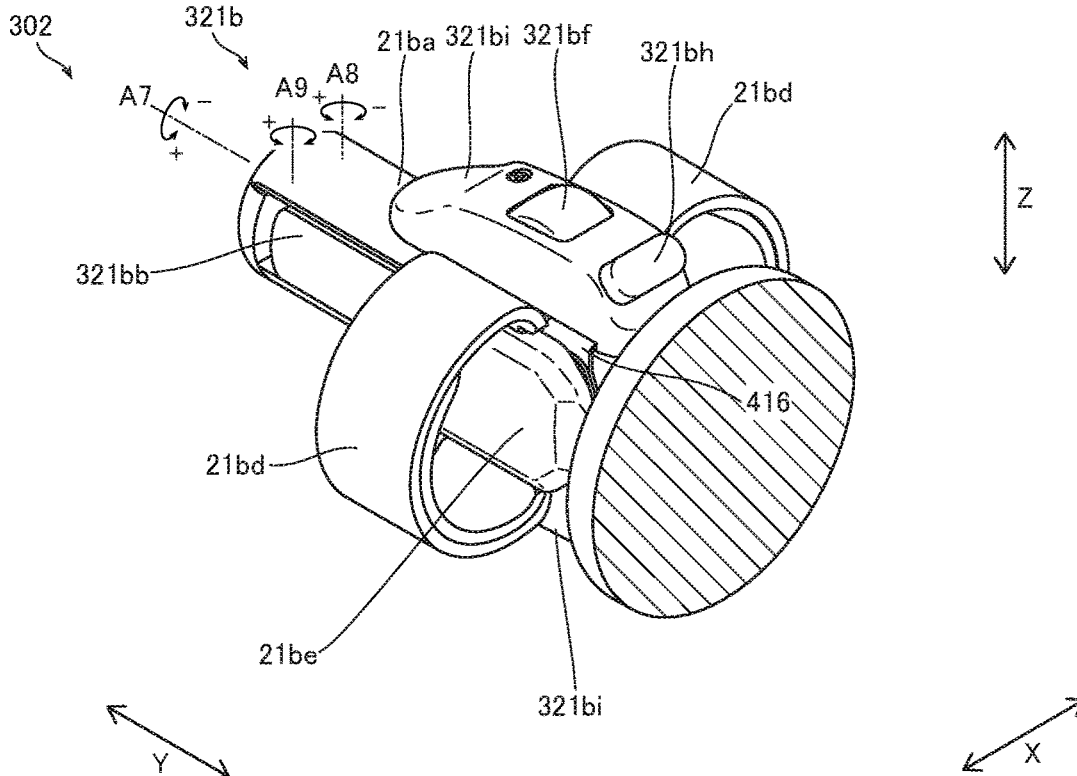
FIG. 8 is a perspective view (2) showing the configuration of the operation handle according to the present embodiment.
Figure 9:
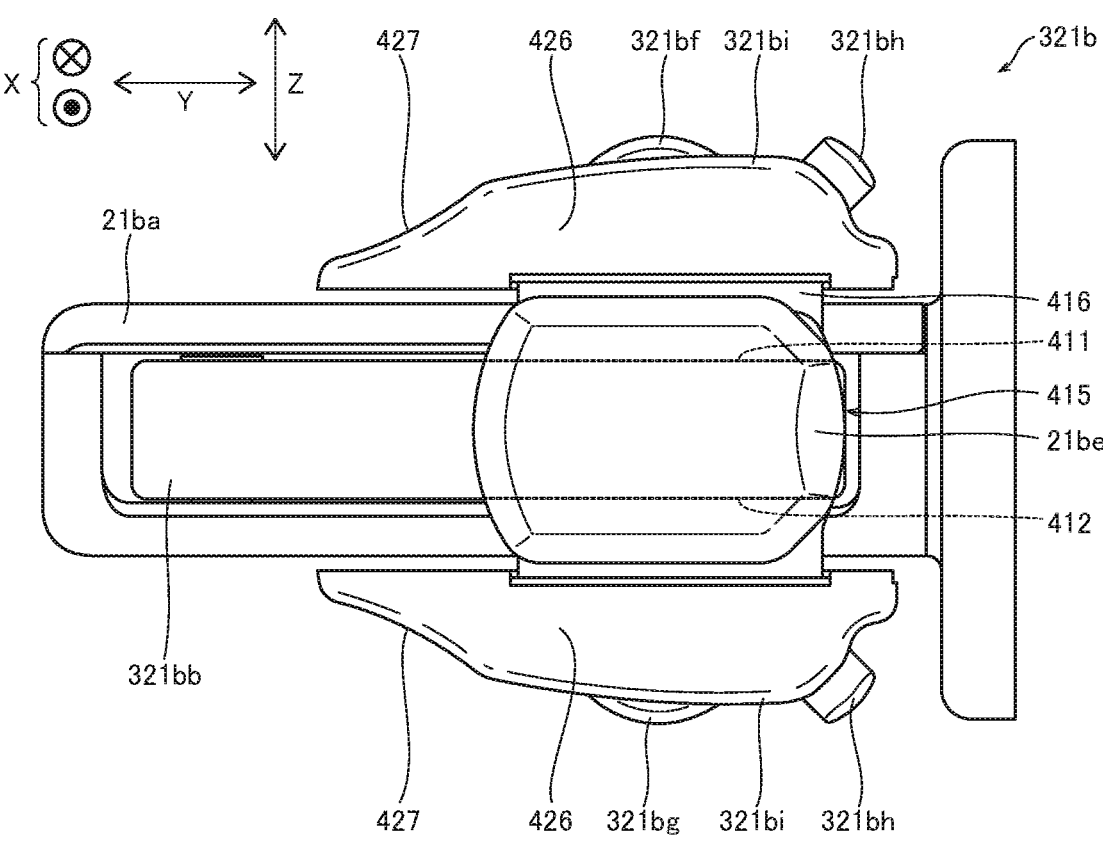
FIG. 9 is a side view showing the configuration of the operation handle according to the present embodiment.

As shown in FIGS. 7 to 9, the first switch 321bf is arranged closer to the distal end than the proximal end of the first lever member 321bb. Specifically, the first switch 321bf is arranged at the position of the distal end of the first lever member 321bb. Furthermore, the first switch 321bf is arranged at a first end 411 of the first end 411 and a second end 412 of the first lever member 321bb in a Z direction parallel to the A9 axis. The first end 411 is a portion of the distal end of the first lever member 321bb on a first side in the Z direction parallel to the A9 axis. The second end 412 is a portion of the distal end of the first lever member 321bb on a second side opposite to the first end 411 in the Z direction parallel to the A9 axis.

The operation handle 321b further includes a second switch 321bg attached to the first lever member 321bb to perform a predetermined function. The first switch 321bf and the second switch 321bg are arranged on the first lever member 321bb. The second switch 321bg has the same function as that of the first switch 321bf. That is, the second switch 321bg is a clutch switch that performs a clutch function of preventing an operation of the operator from being transmitted to the medical manipulator 1. For example, when the operator operates the first lever member 321bb with the index finger of the right hand and operates the second lever member 321bc with the thumb of the right hand, the operator closes the first lever member 321bb and the second lever member 321bc with respect to the support member 21ba (the state shown in FIG. 8), and operates the second switch 321bg with the middle finger of the right hand that is not operating the first lever member 321bb or the second lever member 321bc.

The second switch 321bg is arranged closer to the distal end than the proximal end of the first lever member 321bb. Specifically, the second switch 321bg is arranged at the position of the distal end of the first lever member 321bb. Furthermore, the second switch 321bg is arranged at the second end 412 of the first end 411 and the second end 412 of the first lever member 321bb in the Z direction parallel to the A8 axis. That is, the second switch 321bg is arranged at the second end 412 opposite to the first switch 321bf.

The first switch 321bf and the second switch 321bg are arranged symmetrically with the first lever member 321bb interposed between the first switch 321bf and the second switch 321bg in the Z direction parallel to the A8 axis and the A9 axis. Thus, when the operator prefers to operate the first lever member 321bb with the middle finger of the right hand, the operator can operate the first switch 321bf with the index finger of the right hand that is not operating the first lever member 321bb, and when the operator prefers to operate the first lever member 321bb with the index finger, the operator can operate the first switch 321bf with the middle finger of the right hand that is not operating the first lever member 321bb. Consequently, it is possible to accommodate both an operator who operates the first lever member 321bb with the middle finger of the right hand and an operator who operates the first lever member 321bb with the index finger of the right hand.

The first switch 321bf and the second switch 321bg overlap the support member 21ba in the Z direction parallel to the A8 axis and the A9 axis when the first lever member 321bb is closed with respect to the support member 21ba. Therefore, when the support member 21ba is rotated 180 degrees about the A7 axis with the first lever member 321bb closed with respect to the support member 21ba, the first switch 321bf is located at the position of the second switch 321bg, and the second switch 321bg is located at the position of the first switch 321bf. Thus, even when the support member 21ba is rotated 180 degrees about the A7 axis, the first switch 321bf and the second switch 321bg can be operated in the same manner.

As shown in FIGS. 7 to 10, the first lever member 321bb includes a plate-shaped attachment member 416 attached to an opposing surface 415 of the first lever member 321bb facing the support member 21ba to support the first switch 321bf and the second switch 321bg on support surfaces perpendicular to the opposing surface 415. The attachment member 416 moves integrally with the first lever member 321bb according to rotation of the first lever member 321bb. The attachment member 416 includes a first flat plate 416a parallel to the opposing surface 415, and two second flat plates 416b connected to the first flat plate 416a so as to be bent perpendicularly to the first flat plate 416a. The two second flat plates 416b are connected to a first side and a second side of the first flat plate 416a, respectively, in the Z direction parallel to the A8 axis and the A9 axis. Furthermore, the first switch 321bf and the second switch 321bg are attached to one and the other of the two second flat plates 416b, respectively, so as to be oriented in opposite directions. The two second flat plates 416b support the first switch 321bf and the second switch 321bg on the support surfaces perpendicular to the opposing surface 415. The second flat plates 416b extend from the first flat plate 416a toward the side adjacent to the support member 21ba. The attachment member 416 is not provided on the second lever member 321bc.

Figure 10:
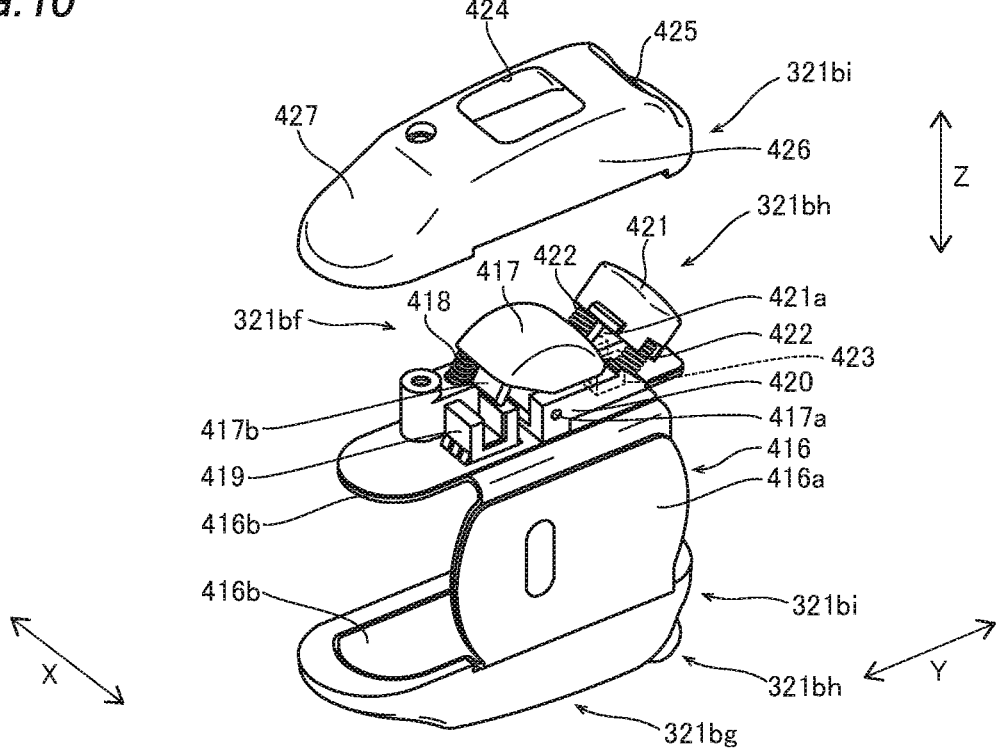
FIG. 10 is an exploded perspective view for illustrating the configuration of switches according to the present embodiment.
Figure 11:
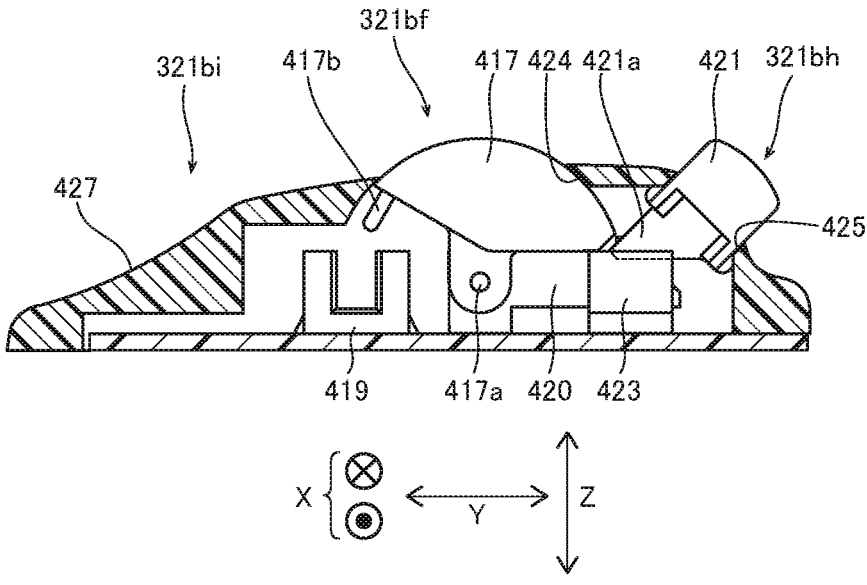
FIG. 11 is a sectional view (1) for illustrating the configuration of the switches according to the present embodiment.
Figure 12:
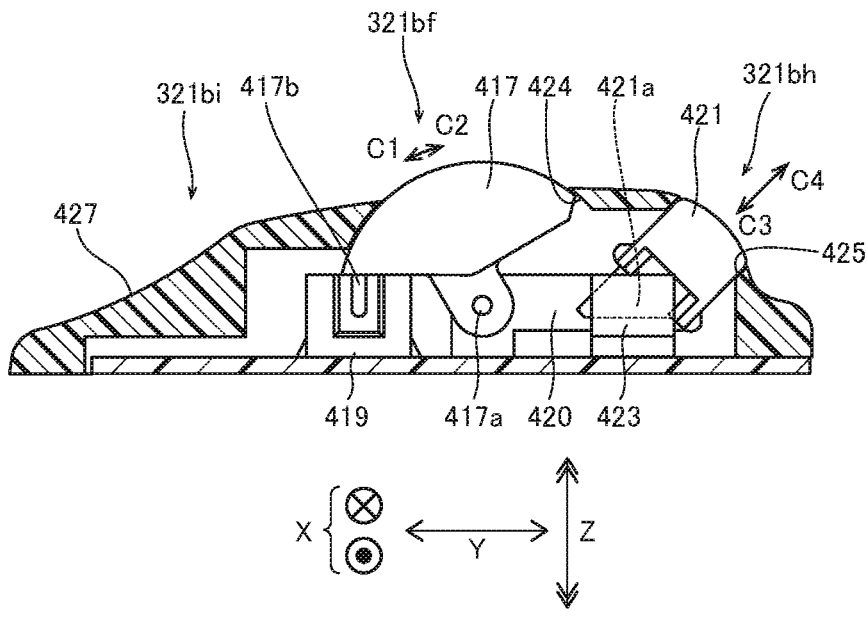
FIG. 12 is a sectional view (2) for illustrating the configuration of the switches according to the present embodiment.
Figure 19:
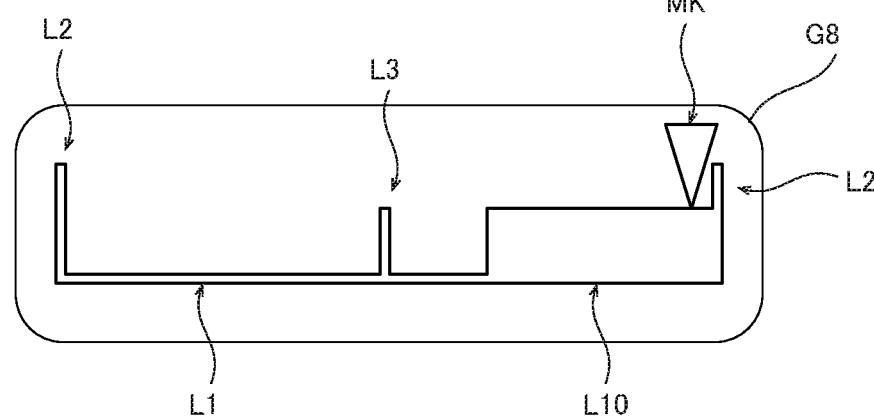
FIG. 19 is a diagram for illustrating a first graphical display.
Figure 20:
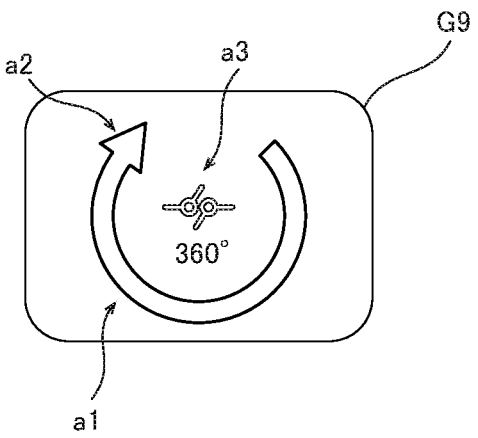
FIG. 20 is a diagram for illustrating a second graphical display.

As shown in FIGS. 10 to 12, the first switch 321bf and the second switch 321bg are roller switches that are rotationally operated by the fingers of the operator. The first switch 321bf and the second switch 321bg as roller switches each include a rotary body 417 that is rotationally operated by the finger of the operator, an urging portion 418 that urges the rotary body 417 to an initial position (a position shown in FIG. 19), and a sensor 419 that detects movement of the rotary body 417. In FIGS. 19 and 20, only the first switch 321*bf* is shown for convenience.

The rotary body 417 has a fan shape and an operation surface curved in an arc. The operation surface of the rotary body 417 slightly protrudes from an opening 424 of a switch housing 321*bi* described below. Furthermore, the rotary body 417 is supported by a support 420 to which a rotation shaft 417*a* is attached via the rotation shaft 417*a* so as to rotate about the rotation shaft 417*a*. The rotary body 417 rotates about the rotation shaft 417*a* between the initial position (the position shown in FIG. 11) not detected by the sensor 419 and a detection position (a position shown in FIG. 12) detected by the sensor 419. The rotary body 417 includes a detected portion 417*b* that is detected by the sensor 419. The detected portion 417*b* has a convex shape protruding toward the sensor 419. The urging portion 418 is an elastic member that urges the rotary body 417 to the initial position. Specifically, the urging portion 418 is a compression coil spring. The sensor 419 is a transmissive photosensor including a light emitter and a light receiver.

As shown in FIGS. 11 and 12, when the operator operates the operation surface of the rotary body 417 by pulling it with his or her finger, the rotary body 417 is rotated to the detection position along a rotation direction C1 about the rotation shaft 417*a* while resisting the urging force of the urging portion 418. At this time, the detected portion 417*b* of the rotary body 417 is inserted between the light emitter and the light receiver of the sensor 419, and light from the light emitter to the light receiver is blocked. Then, the rotary body 417 is detected by the sensor 419. This state is an on-state. In the on-state, the clutch function is performed.

When the operation on the operation surface of the rotary body 417 by the operator is released, the rotary body 417 is rotated to the initial position along a rotation direction C2 opposite to the rotation direction C1 about the rotation shaft 417*a* due to the urging force of the urging portion 418. At this time, the detected portion 417*b* of the rotary body 417 is pulled out from between the light emitter and the light receiver of the sensor 419, and the blocking of the light from the light emitter to the light receiver is released such that passage of the light is allowed. Then, the rotary body 417 is no longer detected by the sensor 419. This state is an off-state. In the off-state, the clutch function is not performed.

In the present embodiment, as shown in FIGS. 7 to 9, the first switch 321*bf* and a third switch 321*bh* are arranged on the operation unit 21*b*. The third switch 321*bh* is a customized switch in which a function to be performed by the customized switch is customized by function setting. Specifically, the first switch 321*bf* and the third switch 321*bh* are arranged on the first lever member 321*bb*. Functions related to the surgery of the patient P, such as image switching and camera zooming, are set to the third switch 321*bh*. Function setting to the third switch 321*bh* is described in detail below. The third switch 321*bh* is an example of a customized switch.

The third switch 321*bh* is inclined with respect to the first switch 321*bf*. Specifically, the third switch 321*bh* is inclined with respect to a Y direction that is the longitudinal direction of the support member 21*ba*. The third switch 321*bh* is positioned more distal than the first switch 321*bf*.

As shown in FIGS. 10 to 12, the third switch 321*bh* is a push-button switch that the operator operates by pressing it with his or her finger. The push-button third switch 321*bh* includes an operation body 421 that the operator operates by pressing it with his or her finger, urging portions 422 that urge the operation body 421 to the initial position (the position shown in FIG. 11), and a sensor 423 that detects movement of the operation body 421. Although FIGS. 11 and 12 show a state in which both the first switch 321*bf* and the third switch 321*bh* are operated for convenience, it is not necessary to operate both the first switch 321*bf* and the third switch 321*bh* at the same time. The first switch 321*bf* and the third switch 321*bh* can be operated independently of each other.

The operation body 421 has an operation surface inclined with respect to the first switch 321*bf*. The operation surface of the operation body 421 protrudes in an inclination direction from an opening 425 of the switch housing 321*bi* described below. Furthermore, the operation body 421 is supported so as to move in the inclination direction. The operation body 421 moves in the inclination direction between the initial position (the position shown in FIG. 11) not detected by the sensor 423 and the detection position (the position shown in FIG. 12) detected by the sensor 423. The operation body 421 includes a detected portion 421*a* that is detected by the sensor 423. The detected portion 421*a* has a convex shape protruding toward the sensor 423. The urging portions 422 are elastic members that urge the operation body 421 to the initial position. Specifically, the urging portions 422 are compression coil springs. The sensor 423 is a transmissive photosensor including a light emitter and a light receiver.

As shown in FIGS. 11 and 12, when the operator operates the operation surface of the operation body 421 by pressing it with his or her finger, the operation body 421 is linearly moved to the detection position along an inclination direction C3 while resisting the urging force of the urging portion 422. At this time, the detected portion 421*a* of the operation body 421 is inserted between the light emitter and the light receiver of the sensor 423, and light from the light emitter to the light receiver is blocked. Then, the operation body 421 is detected by the sensor 423. This state is an on-state. Then, the function having been set to the third switch 321*bh* is performed.

When the operation on the operation surface of the operation body 421 by the operator is released, the operation body 421 is linearly moved to the initial position along an inclination direction C4 opposite to the inclination direction C3 due to the urging force of the urging portion 422. At this time, the detected portion 421*a* of the operation body 421 is pulled out from between the light emitter and the light receiver of the sensor 423, and the blocking of the light from the light emitter to the light receiver is released such that passage of the light is allowed. Then, the operation body 421 is no longer detected by the sensor 423. This state is an off-state. Then, the function having been set to the third switch 321*bh* is not performed. In the third switch 321*bh*, the on-state and the off-state may be reversed. That is, in the off-state, the operation body 421 may be detected by the sensor 423, and in the on-state, the operation body 421 may not be detected by the sensor 423. Alternatively, the third switch 321*bh* may be switched between the on-state and the off-state each time the operation body 421 is detected by the sensor 423.

In the present embodiment, as shown in FIGS. 10 to 12, the third switch 321*bh* and the first switch 321*bf* are arranged in one switch housing 321*bi*. The switch housing 321*bi* includes a finger rest on which the fingers of the operator are placed. The switch housing 321*bi* is arranged on the first lever member 321*bb* that is operated by the index finger or middle finger of the operator. That is, in the present embodiment, the remote control apparatus 2 includes the finger rest attached to the first lever member 321*bb* and on which the fingers of the operator are placed. The switch housing 321*bi* is an example of a housing.

The switch housing 321*bi* covers the first switch 321*bf* and the third switch 321*bh* from the first side in the Z direction parallel to the A8 axis and the A9 axis. The switch housing 321*bi* has a shape extending in the Y direction that is the longitudinal direction of the support member 21*ba*. The switch housing 321*bi* includes the opening 424 in which the first switch 321*bf* is arranged, and the opening 425 in which the third switch 321*bh* is arranged.

The switch housing 321*bi* has a side surface portion 426 and an inclined surface portion 427 as portions that function as finger rests. The side surface portion 426 is a side surface portion arranged on the first lever member 321*bb* side of the switch housing 321*bi* in an X direction, and extends in the Z direction parallel to the A8 axis and the A9 axis and in the Y direction that is the longitudinal direction of the support member 21*ba*. The operator can rest the index finger of the right hand that is not operating the first lever member 321*bb* by placing it on the side surface portion 426 from the side while placing the middle finger of the right hand on the first lever member 321*bb*. The inclined surface portion 427 is positioned more proximal than the openings 424 and 425 in the Y direction, and is inclined with respect to the Y direction. Specifically, the inclined surface portion 427 is inclined so as to be depressed from the first side to the second side in the Z direction. The operator can rest the index finger of the right hand that is not operating the first lever member 321*bb* by placing it on the inclined surface portion 427 from the first side in the Z direction while placing the middle finger of the right hand on the first lever member 321*bb*. Both the side surface portion 426 and the inclined surface portion 427 are portions of the switch housing 321*bi* in which the first switch 321*bf* and the third switch 321*bh* are not arranged, and even when the operator places and rests his or her fingers on the side surface portion 426 and the inclined surface portion 427, there is no risk of erroneously operating the first switch 321*bf* and the third switch 321*bh*.

A third switch 321*bh* is also arranged for the second switch 321*bg*. The configurations of the third switch 321*bh* and a switch housing 321*bi* regarding the second switch 321*bg* are the same as or similar to the configurations of the third switch 321*bh* and the switch housing 321*bi* regarding the first switch 321*bf*.

The operator can place and rest his or her fingers on the switch housing 321*bi* arranged for the second switch 321*bg*, as described below. That is, the operator can rest the ring finger of the right hand that is not operating the first lever member 321*bb* by placing it on a side surface portion 426 from the side while placing the middle finger of the right hand on the first lever member 321*bb*. Furthermore, the operator can rest the middle finger of the right hand that is not operating the first lever member 321*bb* by placing it on the side surface portion 426 from the side while placing the index finger of the right hand on the first lever member 321*bb*. Similarly, the operator can rest the ring finger of the right hand that is not operating the first lever member 321*bb* by placing it on an inclined surface portion 427 from the second side in the Z direction while placing the middle finger of the right hand on the first lever member 321*bb*. Furthermore, the operator can rest the middle finger of the right hand that is not operating the first lever member 321*bb* by placing it on the inclined surface portion 427 from the second side in the Z direction while placing the index finger of the right hand on the first lever member 321*bb*.

Although the first switch 321*bf*, the second switch 321*bg*, and the third switch 321*bh* provided on the operation handle 321*b* of the right-hand operation manipulator 21R have been described, the operation handle 321*b* of the left-hand operation manipulator 21L has the same or similar structure as that of the operation handle 321*b* of the right-hand operation manipulator 21R, except that the operation handle 321*b* of the left-hand operation manipulator 21L has a structure bilaterally symmetrical to that of the operation handle 321*b* of the right-hand operation manipulator 21R. The manipulator arm 60 operated by the right-hand operation manipulator 21R and the manipulator arm 60 operated by the left-hand operation manipulator 21L may be clutched independently of each other by the first switch 321*bf* of the right-hand operation manipulator 21R and the first switch 321*bf* of the left-hand operation manipulator 21L. That is, when the first switch 321*bf* of the right-hand operation manipulator 21R is operated, the manipulator arm 60 operated by the right-hand operation manipulator 21R may be clutched, and when the first switch 321*bf* of the left-hand operation manipulator 21L is operated, the manipulator arm 60 operated by the left-hand operation manipulator 21L may be clutched.

Figure 13:
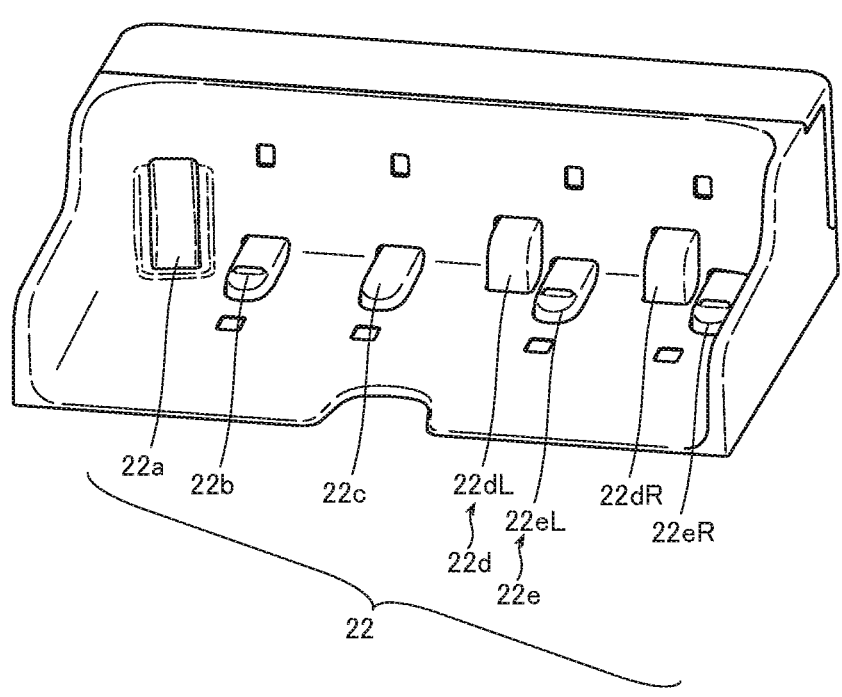
FIG. 13 is a perspective view showing operation pedals according to the present embodiment.

The operation pedals 22 operated by the foot of the operator are now described with reference to FIG. 13. A plurality of operation pedals 22 are provided to perform functions related to the surgical instrument 4. The operation pedals 22 include a switching pedal 22*a*, a clutch pedal 22*b*, a camera pedal 22*c*, an incision pedal 22*d*, and a coagulation pedal 22*e*. The switching pedal 22*a*, the clutch pedal 22*b*, the camera pedal 22*c*, the incision pedal 22*d*, and the coagulation pedal 22*e* are operated by the foot of the operator. The incision pedal 22*d* includes an incision pedal 22*d*R for a right manipulator arm 60, and an incision pedal 22*d*L for a left manipulator arm 60. The coagulation pedal 22*e* includes a coagulation pedal 22*e*R for the right manipulator arm 60 and a coagulation pedal 22*e*L for the left manipulator arm 60.

The switching pedal 22*a* switches the manipulator arms 60 to be operated by the operation units 21*b*. The clutch pedal 22*b* performs a clutch function of preventing an operation of the operator from being transmitted to the medical manipulator 1. While the clutch pedal 22*b* is being pressed by the operator, operations by the operation units 21*b* are not transmitted to the manipulator arms 60. While the camera pedal 22*c* is being pressed by the operator, the operation unit 21*b* can operate the manipulator arm 60 to which the endoscope 4*b* is attached. While the incision pedal 22*d* or the coagulation pedal 22*e* is being pressed by the operator, an electrosurgical device is activated.

The first switch 321*bf* performs a function different from the clutch function that is a predetermined function, by being operated simultaneously with the camera pedal 22*c*. Specifically, the first switch 321*bf* performs a function related to the image GR21 captured by the endoscope 4*b* by being operated simultaneously with the camera pedal 22*c*. When the first switch 321*bf* is operated simultaneously with the camera pedal 22*c*, the first switch 321*bf* performs different functions depending on how the first switch 321*bf* is operated. More specifically, when the first switch 321*bf* is operated simultaneously with the camera pedal 22*c*, the first switch 321*bf* performs different functions depending on at least one of the operation time of the first switch 321*bf* or the number of operations of the first switch 321*bf*.

For example, when the first switch 321bf is operated simultaneously with the camera pedal 22c, the first switch 321bf performs a function of switching the image GR21 captured by the endoscope 4b when a long press operation is performed in which the operation time of the first switch 321bf is equal to or longer than a predetermined time. For example, in a surgery performed by administering indocyanine green (ICG), which is a fluorescent substance, to the patient P, an ICG fluorescence image and a normal image that is not an ICG fluorescence image are switched.

For example, when the first switch 321bf is operated simultaneously with the camera pedal 22c, the first switch 321bf performs a function of zooming in on the image GR21 captured by the endoscope 4b when a short press operation is performed in which the operation time of the first switch 321bf is less than the predetermined time. Furthermore, for example, when the first switch 321bf is operated simultaneously with the camera pedal 22c, the first switch 321bf performs a function of zooming out of the image GR21 captured by the endoscope 4b when a short press operation is performed twice in which the operation time of the first switch 321bf is less than the predetermined time.

The right-hand first switch 321bf and the left-hand first switch 321bf may perform different functions when the camera pedal 22c is operated simultaneously. For example, when the camera pedal 22c and the right-hand first switch 321bf are operated simultaneously, the right-hand first switch 321bf may perform the function of zooming in on the image GR21 captured by the endoscope 4b, and when the camera pedal 22c and the left-hand first switch 321bf are operated simultaneously, the left-hand first switch 321bf may perform the function of zooming out of the image GR21 captured by the endoscope 4b.

Function Setting to Third Switch

Figure 14:
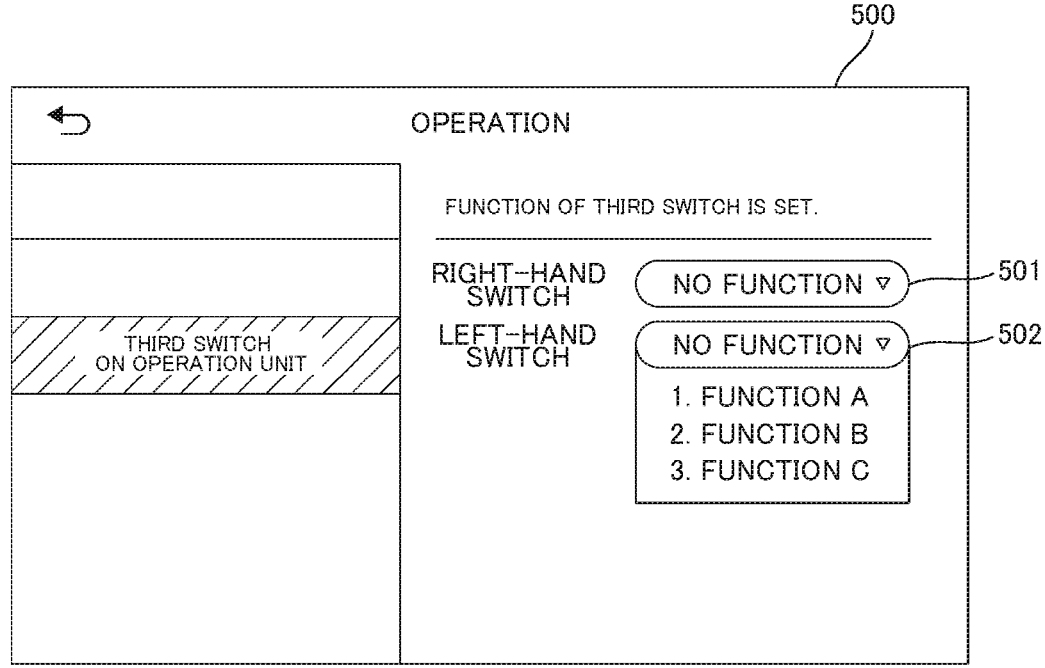
FIG. 14 is a diagram showing a setting screen for setting a function to a third switch.

In the present embodiment, as shown in FIG. 14, a setting screen 500 for setting a function to the third switch 321bh is displayed on the touch panel 23 of the remote control apparatus 2. The setting screen 500 includes a function selection field 501 for the right-hand third switch 321bh and a function selection field 502 for the left-hand third switch 321bh. A process to display the setting screen 500 is performed by the controller 8.

In the present embodiment, a plurality of predetermined functions are displayed on the setting screen 500. A function selected by the operator from among the plurality of functions is set to the third switch 321bh. Specifically, the controller 8 performs a process to display the plurality of predetermined functions on the setting screen 500. The function selection field 501 is a field for selecting a function to be set to the right-hand third switch 321bh. In the function selection field 501, a plurality of functions to be set to the right-hand third switch 321bh are selectably displayed in a pull-down format. An arbitrary function selected by the operator from among the plurality of functions displayed in a pull-down format in the function selection field 501 is set to the right-hand third switch 321bh. A process to set a function to the right-hand third switch 321bh is performed by the controller 8.

The function selection field 502 is a field for selecting a function to be set to the left-hand third switch 321bh. In the function selection field 502, a plurality of functions to be set to the left-hand third switch 321bh are selectably displayed in a pull-down format. An arbitrary function selected by the operator from among the plurality of functions displayed in a pull-down format in the function selection field 502 is set to the left-hand third switch 321bh. A process to set a function to the left-hand third switch 321bh is performed by the controller 8.

In the present embodiment, the surgical system 100 includes the storage 32 shown in FIG. 1. When the surgical system 100 is powered on, a last set function is read from the storage 32 and set to the third switch 321bh. That is, when a function is set for the third switch 321bh on the touch panel 23, the set function is stored in the storage 32. Specifically, the storage 32 stores the function set to the right-hand third switch 321bh and the function set to the left-hand third switch 321bh. Then, when the surgical system 100 is powered on next time, the controller 8 performs the process to set the function stored in the storage 32 to the third switch 321bh. The controller 8 performs a process to perform the function having been set to the third switch 321bh when the third switch 321bh is pressed by the operator.

Pivot Distance Display

Figure 15:
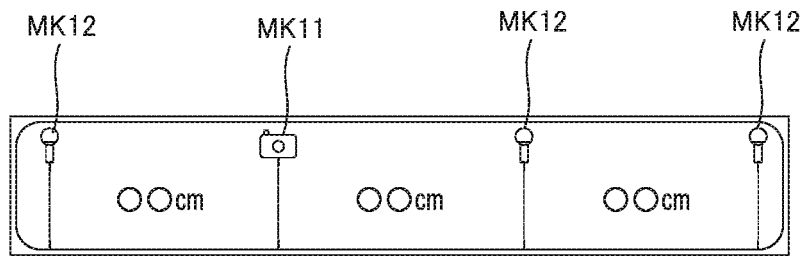
FIG. 15 is a diagram for illustrating a pivot distance display.

In the present embodiment, as shown in FIG. 15, the function to be set to the third switch 321bh includes a function of displaying, on the display, a distance between the pivot positions PP that serve as fulcrums for movement of the surgical instruments 4 attached to the plurality of manipulator arms 60. The distance between the pivot positions PP is displayed on the monitor 24 that is arranged on the remote control apparatus 2 and displays the image GR21 captured by the endoscope 4b, and the display 8b that displays the image GR21 captured by the endoscope 4b. The same image is displayed on the monitor 24 and the display 8b. The process to display the distance between the pivot positions PP on the monitor 24 and the display 8b is performed by the controller 8. Specifically, the pivot positions PP are set for the plurality of manipulator arms 60. The controller 8 performs a process to display, on the monitor 24 and the display 8b, a mark MK11 indicating the manipulator arm 60 corresponding to the endoscope 4b and marks MK12 corresponding to the surgical instruments 4 other than the endoscope 4b. The distance between the pivot positions PP of the manipulator arms 60 is displayed in cm between the marks MK11 and MK12 or between the marks MK12, for example. The distance between the pivot positions PP is displayed after setting of the pivot positions PP and before following operations. The following operations are operations in which the manipulator arms 60 are moved by the operator operating the operation units 21b. While the enable switch 81 of the arm operation unit 80 is being pressed, the distance between the pivot positions PP is not displayed. The distance between the pivot positions PP is displayed on the monitor 24 and the display 8b by turning on the third switch 321bh. The display of the distance between the pivot position PP on the monitor 24 and the display 8b is turned off by turning off the third switch 321bh.

Screen Layout

Figure 16:
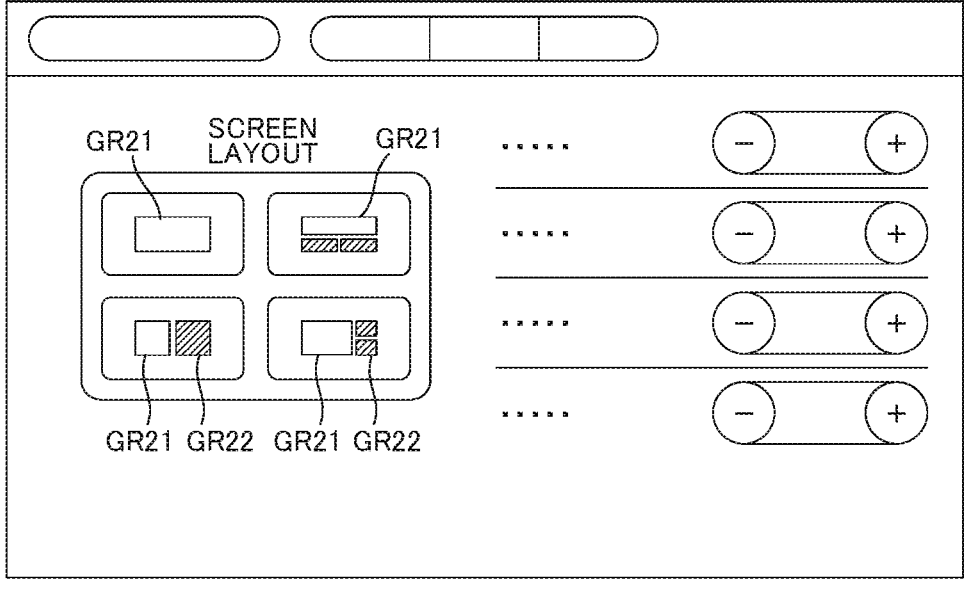
FIG. 16 is a diagram for illustrating a screen layout.

In the present embodiment, as shown in FIG. 16, the function to be set to the third switch 321bh includes a function of switching between displaying the image GR21 captured by the endoscope 4b in full-screen on the monitor 24 and the display 8b and displaying the image GR21 and an image GR22 input from the outside side by side on the monitor 24 and the display 8b. A process to switch between displaying the image GR21 in full-screen and displaying the image GR21 and the image GR22 input from the outside side by side is performed by the controller 8. As shown in FIG. 1, the image GR22 includes an image input from an external device 8e connected to the controller 8 that processes the image GR21 captured by the endoscope 4b. The external device 8e includes an external storage device such as a USB (registered trademark) memory, or a medical imaging device such as a CT device or an MRI device, for example. The image input from the external device 8*e* is an examination image of the patient P, for example.

In the present embodiment, as shown in FIG. 16, the function to be set to the third switch 321*bh* includes a function of switching between displaying the image GR21 captured by the endoscope 4*b* in full-screen on the monitor 24 and the display 8*b*, displaying the image GR21 and the image GR22 side by side in a lateral direction on the monitor 24 and the display 8*b*, and displaying the image GR21 and the image GR22 side by side in a longitudinal direction on the monitor 24 and the display 8*b*. A process to switch between displaying the image GR21 in full-screen, displaying the image GR21 and the image GR22 side by side in the lateral direction, and displaying the image GR21 and the image GR22 side by side in the longitudinal direction is performed by the controller 8. Specifically, each time the third switch 321*bh* is pressed by the operator, displaying the image GR21 in full-screen, displaying the image GR21 and two images GR22 side by side in the longitudinal direction, displaying the image GR21 and one image GR22 side by side in the lateral direction, and displaying the image GR21 and two images GR22 side by side in the lateral direction are switched in order. FIG. 16 shows a screen displayed on the touch panel 23 of the remote control apparatus 2, and the screen layout can also be switched using the touch panel 23.

Operation Handle Position Display

Figure 17:
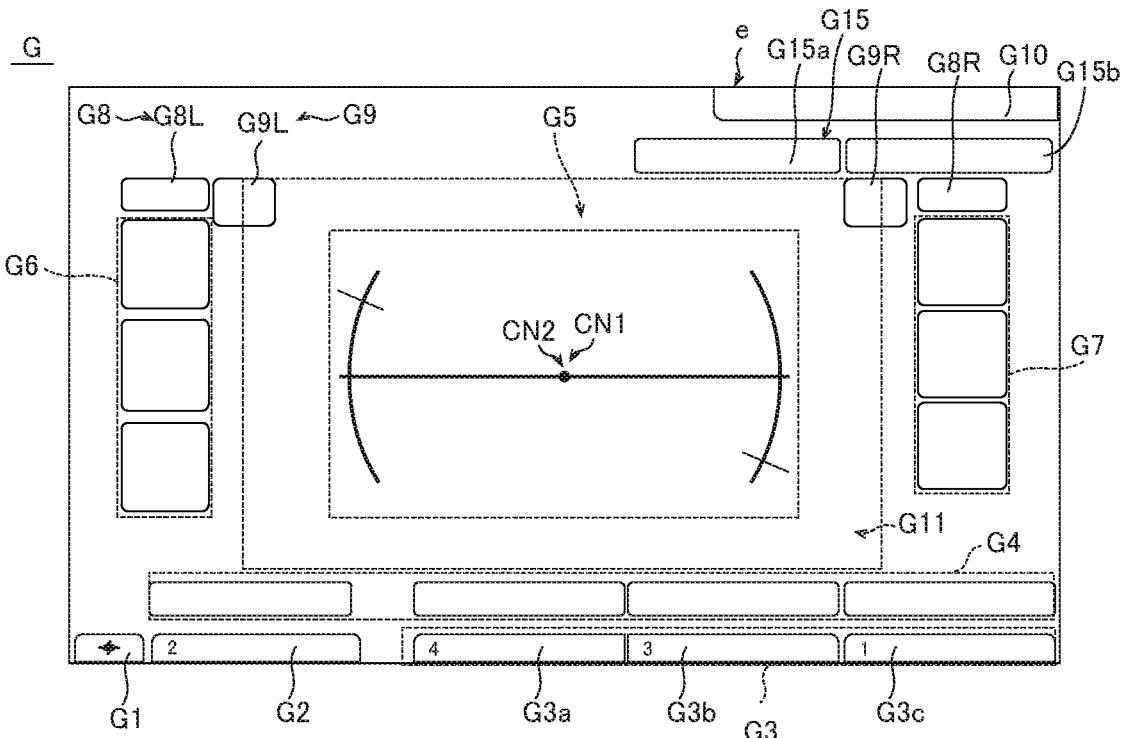
FIG. 17 is a diagram showing areas of a graphical user interface.
Figure 18:
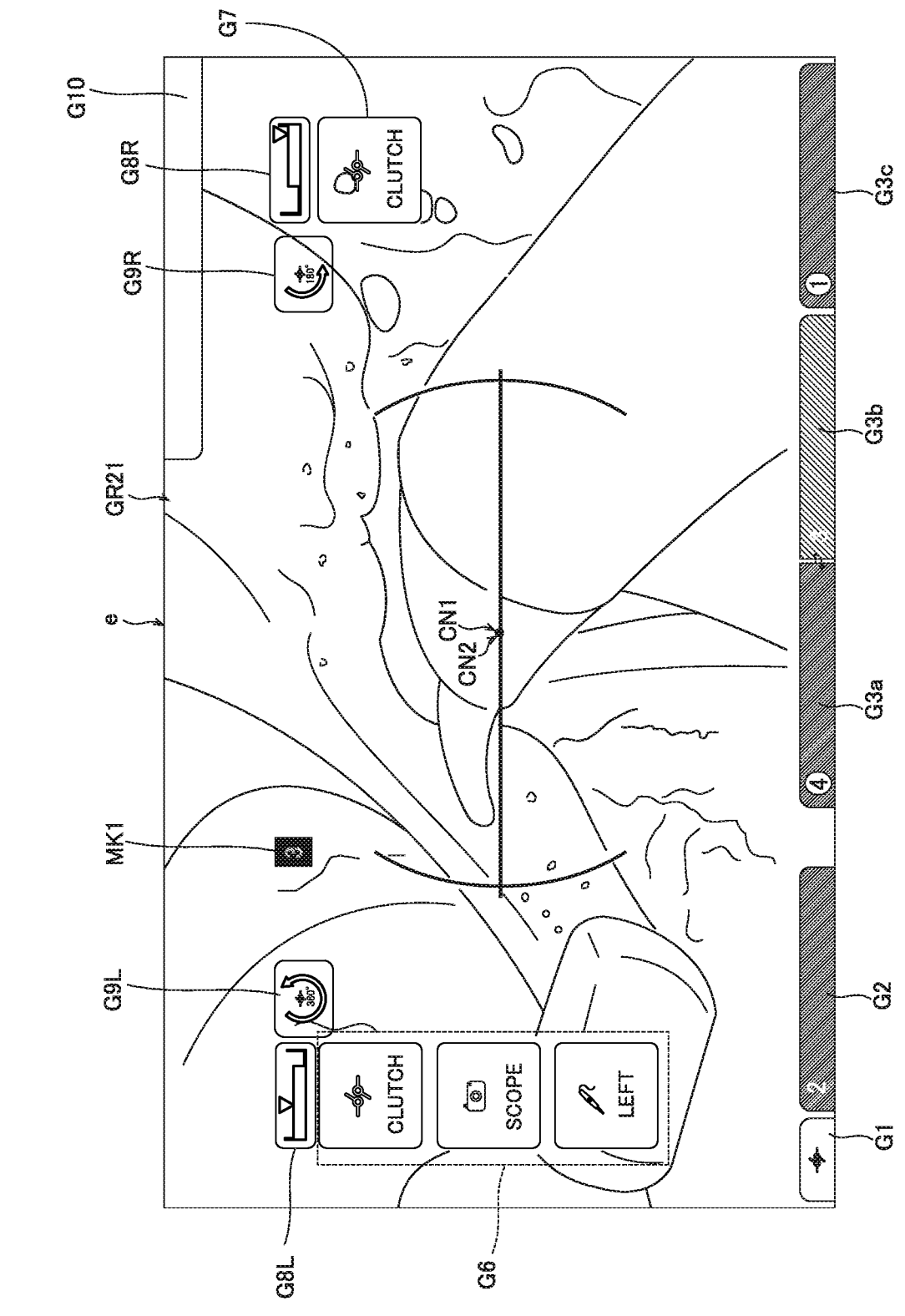
FIG. 18 is a diagram showing an image captured by an endoscope and the graphical user interface.

In the present embodiment, the controller 8 generates a graphical user interface G, as shown in FIG. 17, superimposes the graphical user interface G on the image GR21 captured by the endoscope 4*b*, and displays the graphical user interface G and the image GR21 on the monitor 24 and the display 8*b*, as shown in FIG. 18. The controller 8 captures the image GR21 from the endoscope 4*b*. The controller 8 also acquires information on the movable range of the manipulator arm 60 and information on the current position of the manipulator arm 60 from an arm controller 31*a*. The controller 8 also acquires information on the operable ranges of the operation units 21*b* and information on the current positions of the operation units 21*b* from the remote control apparatus 2.

As shown in FIG. 17, the graphical user interface G shows the state of the clutch pedal 22*b*.

As shown in FIG. 17, the graphical user interface G includes a camera area G2. In the camera area G2, the state of the camera pedal 22*c* is displayed.

As shown in FIG. 17, the graphical user interface G includes a hand area G3. In the hand area G3, the state of each manipulator arm 60 and the states of the coagulation pedal 22*e* and the incision pedal 22*d* are displayed. A clutch area G1, the camera area G2, and the hand area G3 are displayed on the lower side of the monitor 24.

As shown in FIG. 17, the graphical user interface G includes a surgical instrument area G4. In the surgical instrument area G4, the current number of times of use/the maximum number of times of use of the surgical instrument 4 attached to each manipulator arm 60 is displayed. When the current number of uses of the surgical instrument 4 becomes equal to the maximum number of uses of the surgical instrument 4, the current number of uses is displayed in red. When the surgical instrument 4 is not attached to the manipulator arm 60, nothing is displayed in the surgical instrument area G4. The surgical instrument area G4 is displayed on the upper side of the clutch area G1, the camera area G2, and the hand area G3 on the monitor 24.

As shown in FIG. 17, the graphical user interface G includes a level indication area G5. In the level indication area G5, information on the angle of the endoscope 6 is displayed. The level indication area G5 is displayed only while the camera pedal 22*c* is being pressed.

As shown in FIG. 17, the graphical user interface G includes a left pop-up area G6. In the left pop-up area G6, icons are displayed in a hover state in which the foot is placed on the operation pedal 22.

As shown in FIG. 17, the graphical user interface G includes a right pop-up area G7. In the right pop-up area G7, an icon is displayed when the foot is placed on the coagulation pedal 22*e*R or the incision pedal 22*d*R. The right pop-up area G7 is displayed in a right-side portion on the monitor 24.

As shown in FIG. 17, the graphical user interface G includes a first area G8 to display a first graphical display GR1 shown in FIG. 19 and indicating the movable range of the manipulator arm 60 and the operable range in the movable range of the manipulator arm 60, in which the manipulator arm 60 is operable by the operation unit 21*b*. The graphical user interface G also includes a second area G9 different from the first area G8 to display a second graphical display GR2 shown in FIG. 20 and indicating an operation on the operation unit 2*b* required to return the operation unit 21*b* to within the operable range and/or to return the manipulator arm 60 to within the movable range.

In the present embodiment, the function to be set to the third switch 321*bh* includes a function of displaying, on the monitor 24 and the display 8*b*, the graphical user interface G including the first area G8 to display the first graphical display GR1 indicating the movable range of the manipulator arm 60 and the operable range in the movable range of the manipulator arm 60, in which the manipulator arm 60 is operable by the operation unit 21*b*. Furthermore, the function to be set to the third switch 321*bh* includes a function of displaying, on the monitor 24 and the display 8*b*, the graphical user interface G including the second area G9 different from the first area G8 to display the second graphical display GR2 indicating an operation on the operation unit 2*b* required to return the operation unit 21*b* to within the operable range and/or to return the manipulator arm 60 to within the movable range. In the present embodiment, the second graphical display GR2 indicates an operation on the operation unit 21*b* required to return the operation unit 21*b* to within the operable range and to return the manipulator arm 60 to within the movable range. A process to display, on the monitor 24 and the display 8*b*, the graphical user interface G including the first area G8 to display the first graphical display GR1, and a process to display, on the monitor 24 and the display 8*b*, the graphical user interface G to display the second graphical display GR2 are performed by the controller 8. A state in which the first graphical display GR1 and the second graphical display GR are displayed and a state in which the first graphical display GR1 and the second graphical display GR are not displayed are switched by turning on and off the third switch 321*bh*. A process to switch between the displayed state and the non-displayed state is performed by the controller 8.

The movable range of the manipulator arm 60 refers to the movable range of an axis about which the shaft 4*c* is rotated among JT9 to JT12 axes of the manipulator arm 60, and is set to a rotation angle of 540 degrees having 270 degrees in a positive rotation direction and 270 degrees in a negative rotation direction. The operable range of the operation unit 21*b* refers to a movable range about the A7 axis (JT7 axis), and is set to a rotation angle of 540 degrees having 270 degrees in a positive rotation direction and 270 degrees in a negative rotation direction.

As shown in FIG. 19, each of the movable range of the manipulator arm 60 and the operable range of the operation unit 21*b* is represented by the length of a line. The movable range of the manipulator arm 60 is represented by the length of a line L1 extending horizontally on the monitor 24. At both ends of the line L1 extending horizontally, boundary lines L2 extending vertically are provided. The display of the movable range of the manipulator arm 60 further includes a line L3 extending vertically and indicating the center of the movable range. The operable range of the operation unit 21*b* is represented by a line L10 extending horizontally. The current position of the manipulator arm 60 is represented by a triangular mark MK.

As shown in FIG. 20, the second graphical display GR2 is displayed when the angle to the end of the operable range of the operation unit 21*b* becomes equal to or less than a first threshold and when the angle to the end of the movable range of the manipulator arm 60 becomes equal to or less than a second threshold. Each of the first threshold and the second threshold is 10 degrees, for example.

The second graphical display GR2 indicates a direction in which the operation unit 21*b* is to be rotated. The direction in which the operation unit 21*b* is to be rotated is represented by an arc a1 with an arrow a2 provided at the tip end of the arc a1. The second area G9 further displays an angle at which the operation unit 21*b* is rotated. The second area G9 further displays a graphical display a3 for a clutch operation indicating that the clutch operation is required to temporarily disconnect an operational connection between the manipulator arm 60 and the operation unit 21*b*.

Out-of-View Forceps Position Display

As shown in FIG. 18, the controller 8 superimposes the graphical user interface G for displaying a mark MK1 indicating the surgical instrument 4 located outside the field of view of the endoscope 4*b* on the image GR21 captured by the endoscope 4*b* and displays the graphical user interface G and the image GR21 on the monitor 24. This mark MK1 is displayed when the controller 8 receives a command to enable movement of the endoscope 4*b* and when at least one of the surgical instruments 4 is located outside the field of view of the endoscope 4*b*. Furthermore, this mark MK1 is displayed in an area G11 in the vicinity of the outer edge of the level indication area G5, including a central portion CN1 but not including the vicinity of an end e of the screen of the monitor 24.

The controller 8 acquires the position of the surgical instrument 4 based on the posture and position of the manipulator arm 60. The controller 8 also acquires the imaging direction of the endoscope 4*b* based on the posture and position of the manipulator arm 60. The controller 8 also acquires the angle of view of the endoscope 4*b* based on the zooming state of the endoscope 4*b*. The controller 8 acquires the angle of view of the endoscope 4*b* using a value set as a mechanism of the endoscope 4*b*. Then, the controller 8 acquires the coordinates of the tip end of the surgical instrument 4 with respect to the field of view of the endoscope 4*b* based on information on the field of view of the endoscope 4*b*, the posture and position of the endoscope 6, and the position of the manipulator arm 6. Thus, the controller 8 determines whether or not the surgical instrument 4 is located outside the field of view of the endoscope 4*b*.

In an example shown in FIG. 1, the surgical instruments 4 other than the endoscope 4*b* are attached to the manipulator arms 60*a*, 60*b*, and 60*d* of the manipulator arms 60*a*,

60*b*, 60*c*, and 60*d*. The endoscope 4*b* is attached to the manipulator arm 60*c*. As shown in FIG. 18, the manipulator arms 60*a*, 60*b*, and 60*d* correspond to numeral 4 of a hand area G3*a*, numeral 3 of a hand area G3*b*, and numeral 1 of a hand area G3*c*, respectively. The manipulator arm 60*a* corresponds to numeral 2 of the camera area G2. A manner in which it is displayed that the manipulator arms 60 can be operated by the operation units 21*b* and a manner in which it is displayed that the manipulator arms 60 cannot be operated by the operation units 21*b* are different from each other. The display manner is the density of a display color, for example. In FIG. 18, the manipulator arms 60*a* and 60*d* can be operated by the operation units 21*b*, and the hand areas G3*a* and G3*c* are displayed in dark gray. The manipulator arm 60*b* cannot be operated by the operation unit 21*b*, and the hand area G3*b* is displayed in light gray.

In an example shown in FIG. 18, the surgical instruments 4 supported by the manipulator arm 60*a* and the manipulator arm 60*d* are located within the field of view of the endoscope 4*b*. On the other hand, the surgical instrument 4 supported by the manipulator arm 60*b* corresponding to numeral 3 of the hand area G3*b* is located outside the field of view of the endoscope 4*b*.

As shown in FIG. 18, the graphical user interface G displays the mark MK1 indicating the surgical instrument 4 outside the field of view in the area G11 in the vicinity of the outer edge and in a region corresponding to a direction in which the surgical instrument 4 outside the field of view is located with respect to the center CN2 of the level indication area G5.

Figure 21:
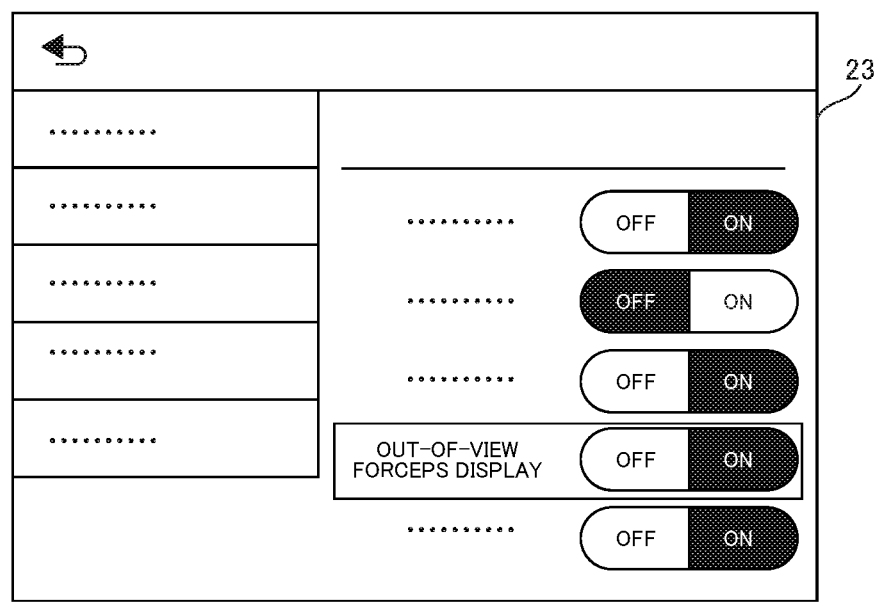
FIG. 21 is a diagram for illustrating a display on a touch panel of the remote control apparatus.

The mark MK1 is switchable between a displayed state and a non-displayed state. A process to switch between display and non-display of the mark MK1 is performed by the controller 8. Specifically, as shown in FIG. 21, a button for out-of-view forceps display is displayed by operating the touch panel 23 of the remote control apparatus 2. When the out-of-view forceps display is selected to be turned on, and the camera pedal 22*c* is pressed by the operator, the mark MK1 is displayed when there is a surgical instrument 4 located outside the field of view of the endoscope 4*b*. When the out-of-view forceps display is selected to be turned off, the mark MK1 is not displayed. Thus, the display setting of the out-of-view forceps display can be easily changed depending on the operating skill level of the operator and the needs of the operator.

In the present embodiment, the function to be set to the third switch 321*bh* includes a function of superimposing the graphical user interface G for displaying the mark MK1 indicating at least one of the surgical instruments 4 located outside the field of view of the endoscope 4*b* on the image GR21 captured by the endoscope 4*b* and displaying the graphical user interface G and the image GR21 on the monitor 24 and the display 8*b* when at least one of the surgical instruments 4 is located outside the field of view. The mark MK1 indicating the surgical instrument 4 located outside the field of view of the endoscope 4*b* is switched between a displayed state and a non-displayed state by turning on and off the third switch 321*bh*. A process to superimpose the graphical user interface G for displaying the mark MK1 indicating the surgical instrument 4 located outside the field of view on the image GR21 and display the graphical user interface G and the image GR21 on the monitor 24 and the display 8*b* is performed by the controller 8. A process to switch between display and non-display of the mark MK1 based on turning on and off the third switch 321*bh* is performed by the controller 8.

ICG Switching

In the present embodiment, the function to be set to the third switch 321bh includes a function of switching an image displayed on the monitor 24 between a fluorescence image and a normal image that is not a fluorescence image. A process to switch between a fluorescence image and a normal image that is not a fluorescence image is performed by the controller 8. Specifically, the function to be set to the third switch 321bh includes a function of switching the image GR21 captured by the endoscope 4b between an indocyanine green fluorescence image and a normal image that is not an indocyanine green fluorescence image in a surgery performed by administering indocyanine green (ICG), which is a fluorescent substance, to the patient P. When the patient P is injected with indocyanine green and near-infrared light is applied to an affected area of the patient P, cancer emits fluorescence and glows. The indocyanine green fluorescence image is an image in which a cancerous area is represented by fluorescence. The image displayed on the monitor 24 and the display 8b is switched between an indocyanine green fluorescence image and a normal image by turning on and off the third switch 321bh.

Digital Zooming Function

In the present embodiment, the function to be set to the third switch 321bh includes a function of digitally zooming the image GR21 captured by the endoscope 4b. Moreover, a digital zoom factor is changed each time the third switch 321bh is operated by the operator. Specifically, each time the third switch 321bh is turned on, the digital zoom factor is changed in a plurality of stages. For example, each time the third switch 321bh is turned on, the digital zoom factor is changed in four stages. A digital zooming process based on pressing the third switch 321bh is performed by the controller 8.

Error Reset Function

When an error occurs in the surgical system 100, the controller 8 determines whether or not the error that has occurred is recoverable. A recoverable error is reset by pressing any one of the error reset button 26a of the remote control apparatus 2, the error reset button 33a of the input 33, and the error reset button 8c of the controller 8. In the present embodiment, the function to be set to the third switch 321bh includes a function of resetting an error when the error occurs in the surgical system 100. That is, the recoverable error is also reset by pressing the third switch 321bh. An error reset process based on pressing the third switch 321bh is performed by the controller 8. The recoverable error refers to an error with a relatively non-fatal error level, and the surgical system 100 can be continuously used by resetting the error. When an unrecoverable error occurs, the surgical system 100 cannot be continuously used.

Stopping of Alarm Sound

When an error occurs in the surgical system 100, the controller 8 controls a speaker to generate an alarm sound. The function to be set to the third switch 321bh includes a function to stop the alarm sound emitted when the error occurs in the surgical system 100. That is, the alarm sound is stopped by pressing the third switch 321bh. A process to stop the alarm sound based on pressing the third switch 321bh is performed by the controller 8.

Process Flow of Controller

Figure 22:
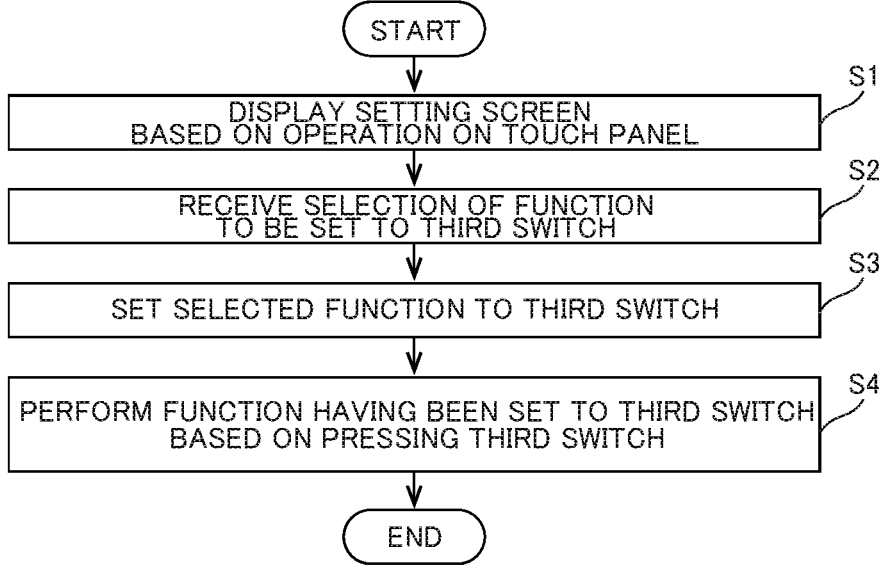
FIG. 22 is a diagram showing a process flow of a controller.

As shown in FIG. 22, in step S1, the controller 8 causes the touch panel 23 of the remote control apparatus 2 to display the setting screen 500 for setting a function to the third switch 321bh based on the touch panel 23 of the remote control apparatus 2 being operated by the operator.

In step S2, the controller 8 receives a selection of one of the plurality of functions displayed on the setting screen 500 based on an operation on the touch panel 23 by the operator. The controller 8 performs a process to store the received function in the storage 32.

In step S3, the controller 8 performs a process to set the function selected by the operator to the third switch 321bh.

In step S4, when the third switch 321bh is pressed by the operator, the controller 8 performs the function having been set to the third switch 321bh.

Advantages of Present Embodiment

The remote control apparatus 2 includes the third switch 321bh arranged on the operation unit 21b and in which a function to be performed by the third switch is customized by function setting by the operator. Accordingly, the operator can set a function desired by the operator as a function to be performed by the third switch 321bh, and thus the function to be performed by the third switch 321bh can be changed. Consequently, the degree of freedom in the function performed by the third switch 321bh arranged on the operation unit 21b can be increased.

The remote control apparatus 2 further includes the touch panel 23 to display the setting screen 500 to set a function to the third switch 321bh. Accordingly, the operator can easily set a function to the third switch 321bh using the setting screen 500.

The surgical system 100 further includes the storage 32 to store a set function. When the surgical system 100 is powered on, the last set function is read from the storage 32 and set to the third switch 321bh. Accordingly, when the surgical system 100 is powered on next time, the function stored in the storage 32 is automatically set to the third switch 321bh, and thus the time and effort of the operator required to set a function to the third switch 321bh can be saved.

The plurality of predetermined functions are displayed on the setting screen 500, and the function selected by the operator is set to the third switch 321bh. Accordingly, the operator can easily select the function to be set to the third switch 321bh on the setting screen 500 of the remote control apparatus 2.

The plurality of manipulator arms 60 are arranged, and the surgical instrument 4 includes the endoscope 4b. The remote control apparatus 2 further includes the monitor 24 to display the image GR21 captured by the endoscope 4b. The function to be set to the third switch 321bh includes the function of displaying, on the monitor 24, the distance between the pivot positions PP that serve as fulcrums for movement of the surgical instruments 4 attached to the plurality of manipulator arms 60. Accordingly, the operator can easily display the distance between the pivot positions PP on the monitor 24 by operating the third switch 321bh.

The surgical system 100 further includes the display 8b to display the image GR21 captured by the endoscope 4b. The display 8b is arranged independently of the medical manipulator 1 and the remote control apparatus 2. Accordingly, the distance between the pivot positions PP is displayed on both the monitor 24 and the display 8b. Consequently, the operator can visually recognize the distance between the pivot positions PP on both the monitor 24 and the display 8b. As a result, the convenience of visually recognizing the distance between the pivot positions PP can be improved.

The surgical instrument 4 includes the endoscope 4b. The remote control apparatus 2 further includes the monitor 24 to display the image GR21 captured by the endoscope 4b. The function to be set to the third switch 321bh includes the function of switching between displaying the image GR21 captured by the endoscope 4*b* in full-screen on the monitor 24 and displaying the image GR21 and the image GR22 input from the external device 8*e* side by side on the monitor 24. Accordingly, the image GR21 is displayed in a large size by displaying the image GR21 in full-screen, and thus the visibility of the image GR21 can be improved. Moreover, the operator can visually recognize not only the image GR21 but also the image GR22 by displaying the image GR21 and the image GR22 side by side.

The image GR22 includes the image input from the external device 8*e* connected to the controller 8 configured or programmed to process the image GR21 captured by the endoscope 4*b*. Accordingly, even an image that is not stored in the surgical system 100 can be displayed on the monitor 24 and the display 8*b* by being input from the external device 8*e*.

The function to be set to the third switch 321*bh* includes the function of switching between displaying the image GR21 captured by the endoscope 4*b* in full-screen on the monitor 24, displaying the image GR21 and the image GR22 side by side in the lateral direction on the monitor 24, and displaying the image GR21 and the image GR22 side by side in the longitudinal direction on the monitor 24. Accordingly, the display format of an image(s) displayed on the monitor 24 can be changed according to the preference of the operator.

The surgical system 100 further includes the monitor 24 to display the image GR21 captured by the endoscope 4*b*, and the controller 8 configured or programmed to generate the graphical user interface G, superimpose the graphical user interface G on the image GR21 captured by the endoscope 4*b*, and display the graphical user interface G and the image GR21 on the monitor 24 and the display 8*b*. The function to be set to the third switch 321*bh* includes the function of displaying, on the monitor 24, the graphical user interface G including the first area G8 to display the first graphical display GR1 indicating the movable range of the manipulator arm 60 and the operable range in the movable range of the manipulator arm 60, in which the manipulator arm 60 is operable by the operation unit 21*b*. Accordingly, the third switch 321*bh* is arranged on the operation unit 21*b*, and thus the operator can perform an operation to display the first graphical display GR1 while performing an operation to move the manipulator arm 60 using the operation unit 21*b*.

The function to be set to the third switch 321*bh* includes the function of displaying, on the monitor 24, the graphical user interface G including the second area G9 different from the first area G8 to display the second graphical display GR2 indicating an operation on the operation unit 2*b* required to return the operation unit 21*b* to within the operable range and/or to return the manipulator arm 60 to within the movable range. Accordingly, the third switch 321*bh* is arranged on the operation unit 21*b*, and thus the operator can perform an operation to display the second graphical display GR2 while performing an operation to move the manipulator arm 60 using the operation unit 21*b*.

The surgical system 100 further includes the controller 8 configured or programmed to generate the graphical user interface G, superimpose the graphical user interface G on the image GR21 captured by the endoscope 4*b*, and display the graphical user interface G and the image GR21 on the monitor 24. The function to be set to the third switch 321*bh* includes the function of displaying, on the graphical user interface G, the mark MK1 indicating at least one of the surgical instruments 4 located outside the field of view of the endoscope 4*b* when at least one of the surgical instruments 4 is located outside the field of view. Accordingly, the third switch 321*bh* is arranged on the operation unit 21*b*, and thus the operator can perform an operation to display the mark MK1 indicating at least one of the surgical instruments 4 located outside the field of view while performing an operation to move the manipulator arm 60 using the operation unit 21*b*.

The surgical system 100 further includes the monitor 24 to display the image GR21 captured by the endoscope 4*b*. The function to be set to the third switch 321*bh* includes the function of switching between the fluorescence image and the normal image that is not the fluorescence image. Accordingly, the third switch 321*bh* is arranged on the operation unit 21*b*, and thus the operator can perform an operation to switch between the fluorescence image and the normal image that is not the fluorescence image while performing an operation to move the manipulator arm 60 using the operation unit 21*b*.

The surgical system 100 further includes the monitor 24 to display the image GR21 captured by the endoscope 4*b*. The function to be set to the third switch 321*bh* includes the function of zooming a digital image captured by the endoscope 4*b*. Accordingly, the third switch 321*bh* is arranged on the operation unit 21*b*, and thus the operator can perform an operation to digitally zoom the image GR21 captured by the endoscope 4*b* while performing an operation to move the manipulator arm 60 using the operation unit 21*b*.

The digital zoom factor is changed each time the third switch 321*bh* is operated by the operator. Accordingly, the operator can change the digital zoom factor according to the preference of the operator by operating the third switch 321*bh*.

The function to be set to the third switch 321*bh* includes the function of resetting the error when the error occurs in the surgical system 100. Accordingly, the third switch 321*bh* is arranged on the operation unit 21*b*, and thus the operator can reset the error without moving to a position spaced apart from the operation unit 21*b*.

The function to be set to the third switch 321*bh* includes the function of stopping the alarm sound emitted when the error occurs in the surgical system 100. Accordingly, the third switch 321*bh* is arranged on the operation unit 21*b*, and thus the operator can stop the alarm sound without moving to a position spaced apart from the operation unit 21*b*.

The operation unit 21*b* includes the support member 21*ba* arranged at the proximal end of the operation unit 21*b*, and the first lever member 321*bb* attached to the support member 21*ba* so as to rotate with respect to the support member 21*ba*, and the third switch 321*bh* is attached to the first lever member 321*bb*. Accordingly, the third switch 321*bh* can be rotated by rotating the first lever member 321*bb*, and thus the third switch 321*bh* can be moved to a position at which the third switch 321*bh* can be easily operated by the operator. Consequently, the third switch 321*bh* can be easily operated, and thus the operability of the third switch 321*bh* can be improved.

The surgical system 100 further includes the switch housing 321*bi* arranged on the first lever member 321*bb* and in which the third switch 321*bh* is arranged. The switch housing 321*bi* functions as a finger rest on which the fingers of the operator are placed. Accordingly, the operator can rest his or her fingers by placing them on the switch housing 321*bi* functioning as a finger rest, and thus fatigue on the fingers of the operator can be mitigated. Furthermore, the switch housing 321*bi* in which the third switch 321*bh* is arranged is used as a finger rest, and thus an increase in the number of components can be reduced or prevented as compared with a case in which a finger rest is provided separately from the switch housing 321*bi*.

According to the present embodiment, as described above, the remote control apparatus 2 includes the first switch 321*bf* attached to the first lever member 321*bb* to perform the predetermined function. Accordingly, when the operator of the remote control apparatus 2 operates the medical manipulator 1 including the manipulator arm 60 having a tip end to which the surgical instrument 4 is attached, the operability of the first switch 21*bf* operated by the hand of the operator can be improved.

According to the present embodiment, as described above, the first switch 321*bf* is a roller switch. Accordingly, the operator can rotationally operate the first switch 321*bf* as a roller switch, and thus the operator can easily operate the first switch 321*bf* as a roller switch.

According to the present embodiment, as described above, the roller switch includes the rotary body 417 rotationally operated by the operator, the urging portion 418 to urge the rotary body 417 to the initial position, and the sensor 419 to detect movement of the rotary body 417. Accordingly, when the operator operates the rotary body 417, movement of the rotary body 417 can be detected by the sensor 419. When the operator does not operate the rotary body 417 or when the operator releases his or her finger after the operation, the urging portion 418 urges the rotary body 417 to the initial position such that the sensor 419 cannot detect movement of the rotary body 417.

According to the present embodiment, as described above, the first switch 321*bf* and the third switch 321*bh* are arranged on the first lever member 321*bb*. Accordingly, the first switch 321*bf* and the third switch 321*bh* are arranged on the first lever member 321*bb*, and thus the operator can selectively use the first switch 321*bf* and the third switch 321*bh*.

According to the present embodiment, as described above, the third switch 321*bh* is inclined with respect to the first switch 321*bf*. Accordingly, the third switch 321*bh* can be operated from a direction inclined with respect to the first switch 321*bf*, and thus erroneous pressing between the third switch 321*bh* and the first switch 321*bf* can be effectively reduced or prevented.

According to the present embodiment, as described above, the remote control apparatus 2 includes the camera pedal 22*c* operated by the foot of the operator. Furthermore, the first switch 321*bf* is operable to perform the function different from the predetermined function by being operated simultaneously with the camera pedal 22*c*. Accordingly, the predetermined function can be performed by the first switch 321*bf*, and the function different from the predetermined function can also be performed by simultaneously operating the first switch 321*bf* and the camera pedal 22*c*. Consequently, the first switch 321*bf* can be effectively used to perform various functions.

According to the present embodiment, as described above, the first switch 321*bf* is operable to perform different functions depending on how the first switch 321*bf* is operated when the first switch 321*bf* is operated simultaneously with the camera pedal 22*c*. Accordingly, different functions can be performed depending on how the first switch 321*bf* is operated when the first switch 321*bf* and the camera pedal 22*c* are operated simultaneously, and thus the first switch 321*bf* can be more effectively used to perform more various functions.

According to the present embodiment, as described above, the first switch 321*bf* is operable to perform different functions depending on at least one of the operation time of the first switch 321*bf* or the number of operations of the first switch 321*bf* when the first switch 321*bf* is operated simultaneously with the camera pedal 22*c*. Accordingly, different functions can be easily performed depending on at least one of the operation time of the first switch 321*bf* or the number of operations of the first switch 321*bf* when the first switch 321*bf* and the camera pedal 22*c* are operated simultaneously.

According to the present embodiment, as described above, the first lever member 321*bb* further includes the plate-shaped attachment member 416 attached to the opposing surface 415 of the first lever member 321*bb* facing the support member 21*ba* to support the first switch 321*bf* perpendicularly to the opposing surface 415. Accordingly, as compared with a case in which the first switch 321*bf* is arranged parallel to the opposing surface 415 of the first lever member 321*bb* facing the support member 21*ba*, the first switch 321*bf* can be easily operated, and thus the operability of the switch 321*bf* can be improved.

According to the present embodiment, as described above, the remote control apparatus 2 includes the switch housing 321*bi* in which the first switch 321*bf* is arranged. Furthermore, the switch housing 321*bi* includes a finger rest on which the fingers of the operator are placed. Accordingly, the operator can rest his or her fingers by placing them on the switch housing 321*bi* as a finger rest, and thus fatigue on the fingers of the operator can be mitigated. Furthermore, the switch housing 321*bi* in which the first switch 321*bf* is arranged is used as a finger rest, and thus an increase in the number of components can be reduced or prevented as compared with a case in which a finger rest is provided separately from the switch housing 321*bi*.

According to the present embodiment, as described above, the switch housing 321*bi* is arranged on the first lever member 321*bb* operated by the index finger or middle finger of the operator. When the operator operates the first lever member 321*bb* with his or her index finger, the middle finger and the ring finger, for example, other than the index finger become the fingers of the operator that can be rested on the finger rest. When the operator operates the first lever member 321*bb* with his or her middle finger, the index finger and the ring finger, for example, other than the middle finger become the fingers of the operator that can be rested on the finger rest. Therefore, with the configuration described above, the switch housing 321*bi* is arranged on the first lever member 321*bb* on the side on which the fingers of the operator that can be rested, other than the finger (index finger or middle finger) of the operator operating the first lever member 321*bb*, are present, and thus the switch housing 321*bi* can be effectively used as a finger rest.

According to the present embodiment, as described above, the first switch 321*bf* and the second switch 321*bg* operable to perform the predetermined function are arranged on the first lever member 321*bb*. Accordingly, the first switch 321*bf* and the second switch 321*bg* are arranged on the first lever member 321*bb*, and thus as compared with a case in which the second switch 321*bg* is arranged on a member other than the first lever member 321*bb*, the complexity of the structure can be reduced or prevented, and the first switch 321*bf* and the second switch 321*bg* can be easily arranged.

Modified Examples

The embodiment disclosed this time must be considered as illustrative in all points and not restrictive. The scope of the present disclosure is not shown by the above description of the embodiment but by the scope of claims for patent, and all modifications (modified examples) within the meaning and scope equivalent to the scope of claims for patent are further included.

For example, while the example in which the operation handle 321*b* includes the first lever member 321*bb* and the second lever member 321*bc* has been shown in the aforementioned embodiment, the present disclosure is not limited to this. For example, the operation handle 321*b* may include only one of the first lever member 321*bb* and the second lever member 321*bc*.

While the example in which the third switch 321*bh* is arranged on the first lever member 321*bb* has been shown in the aforementioned embodiment, the present disclosure is not limited to this. For example, the third switch 321*bh* may be arranged on a portion of the operation unit 21*b* other than the first lever member 321*bb*.

While the example in which the setting screen 500 for setting a function to the third switch 321*bh* is displayed on the touch panel 23 of the remote control apparatus 2 has been shown in the aforementioned embodiment, the present disclosure is not limited to this. In the present disclosure, the setting screen 500 for setting a function to the third switch 321*bh* may be displayed on a display other than the touch panel 23 of the remote control apparatus 2.

Figure 23:
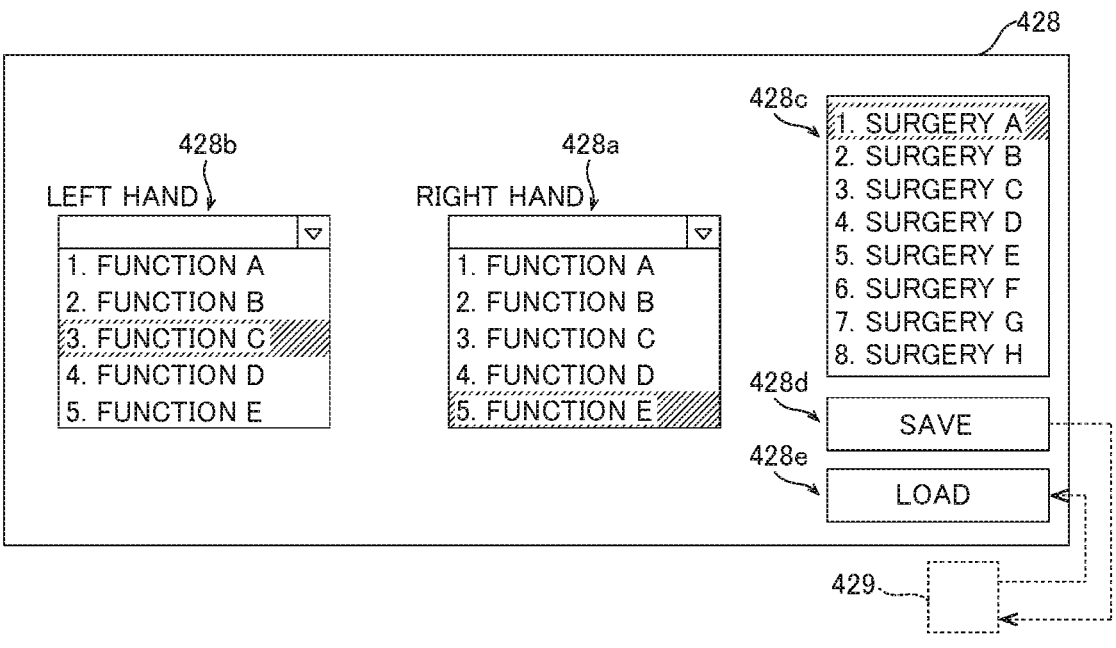
FIG. 23 is a diagram for illustrating a setting screen according to a modified example.

While the example in which the function stored in the storage 32 while the surgical system 100 was powered on last time is set to the third switch 321*bh* when the surgical system 100 is powered on has been shown in the aforementioned embodiment, the present disclosure is not limited to this. For example, the function stored in the storage 32 while the surgical system 100 was powered on last time may be set to the third switch 321*bh* by operating a predetermined switch. Specifically, as shown in FIG. 23, a setting screen 428 is displayed on the touch panel 23 or the monitor 24, for example, when a function is set to the third switch 321*bh*. The setting screen 428 includes function selection fields 428*a* and 428*b*, a surgery name selection field 428*c*, a save button 428*d*, and a load button 428*e*.

The function selection field 428*a* is a field for selecting a function to be set to the right-hand third switch 321*bh*. In the function selection field 428*a*, a plurality of functions to be set to the right-hand third switch 321*bh* are selectably displayed in a pull-down format. An arbitrary function selected by the operator from among the plurality of functions displayed in a pull-down format in the function selection field 428*a* is set to the right-hand third switch 321*bh*.

The function selection field 428*b* is a field for selecting a function to be set to the left-hand third switch 321*bh*. In the function selection field 428*b*, a plurality of functions to be set to the left-hand third switch 321*bh* are selectably displayed in a pull-down format. An arbitrary function selected by the operator from among the plurality of functions displayed in a pull-down format in the function selection field 428*b* is set to the left-hand third switch 321*bh*.

The surgery name selection field 428*c* is a field for selecting a surgery name. In the surgery name selection field 428*c*, a plurality of surgery names are selectably displayed. The function of the right-hand third switch 321*bh* selected in the function selection field 428*a* and the function of the left-hand third switch 321*bh* selected in the function selection field 428*b* are stored in a storage 429 of the remote control apparatus 2 in association with an arbitrary surgery name selected by the operator from among the plurality of surgery names displayed in the surgery name selection field 428*c*. Thus, the functions of the right-hand third switch 321*bh* and the left-hand third switch 321*bh* can be managed for each surgery name displayed in the surgery name selection field 428*c*. The storage 429 is a nonvolatile storage device such as a flash memory.

The save button 428*d* is a button on the display for the operator to save settings. When the save button 428*d* is operated, the function of the right-hand third switch 321*bh* selected in the function selection field 428*a* and the function of the left-hand third switch 321*bh* selected in the function selection field 428*b* are stored as data to be saved in the storage 429 in association with the surgery name selected in the surgery name selection field 428*c*. Furthermore, the remote control apparatus 2 reads last used saved data from the storage 429 when the power is turned on. Thus, when the last used saved data is used, it is not necessary to reset the function of the third switch 321*bh*.

The load button 428*e* is a button on the display for the operator to read the settings. When the load button 428*e* is operated with a surgery name selected in the surgery name selection field 428*c*, the saved data corresponding to the surgery name selected in the surgery name selection field 428*c* is read from the storage 429. Then, the function of the right-hand third switch 321*bh* and the function of the left-hand third switch 321*bh*, which are associated with the surgery name selected in the surgery name selection column 428*c*, are set as the functions of the switches.

While the example in which the function to be set to the third switch 321*bh* includes pivot distance display, screen layout, display of the position of the operation unit 21*b*, display of the position of the out-of-view forceps, ICG switching, zooming function, error reset function, and stopping of the alarm sound has been shown in the aforementioned embodiment, the present disclosure is not limited to this. For example, the function to be set to the third switch 321*bh* may include at least one of the functions described above or may include a function other than the functions described above.

While the example in which both the monitor 24 and the display 8*b* display the pivot distance, the screen layout, the position of the operation unit 21*b*, the position of the out-of-view forceps, the fluorescence image, and the normal image has been shown in the aforementioned embodiment, the present disclosure is not limited to this. The pivot distance, the screen layout, the position of the operation unit 21*b*, the position of the out-of-view forceps, the fluorescence image, and the normal image may be displayed only on the monitor 24.

The functionality of the elements disclosed herein may be implemented using circuitry or processing circuitry that includes general purpose processors, special purpose processors, integrated circuits, application specific integrated circuits (ASICs), conventional circuitry and/or combinations thereof that are configured or programmed to perform the disclosed functionality. Processors are considered processing circuitry or circuitry as they include transistors and other circuitry therein. In the present disclosure, the circuitry, units, or means are hardware that carries out or is programmed to perform the recited functionality. The hardware may be hardware disclosed herein or other known hardware that is programmed or configured to carry out the recited functionality. When the hardware is a processor that may be considered a type of circuitry, the circuitry, means, or units are a combination of hardware and software, and the software is used to configure the hardware and/or processor.

Aspects

It will be appreciated by those skilled in the art that the exemplary embodiments described above are specific examples of the following aspects.

(Item 1)

A robotic surgical system comprising:

a patient-side apparatus including a robot arm having a tip end to which a surgical instrument is attached; and an operator-side apparatus including an operation manipulator including an operation unit to receive an operation for the surgical instrument, the operation manipulator being operable to move the robot arm; wherein the operation unit includes a customized switch in which a function to be performed by the customized switch is customized by function setting by an operator.

(Item 2)

The robotic surgical system according to item 1, wherein the operator-side apparatus further includes a function setting display to display a setting screen to set the function to the customized switch.

(Item 3)

The robotic surgical system according to item 1 or 2, further comprising:

a storage to store a set function; wherein a last set function is read from the storage and set to the customized switch when the robotic surgical system is powered on.

(Item 4)

The robotic surgical system according to item 2 or 3, wherein a plurality of predetermined functions are displayed on the setting screen; and a function selected from among the plurality of functions by the operator is set to the customized switch.

(Item 5)

The robotic surgical system according to any one of items 1 to 4, wherein a plurality of robot arms are arranged, each of which is the robot arm;

the surgical instrument includes an endoscope;

the operator-side apparatus further includes a first display to display an image captured by the endoscope; and the function to be set to the customized switch includes a function of displaying, on the first display, a distance between pivot positions that serve as fulcrums for movement of surgical instruments attached to the plurality of robot arms.

(Item 6)

The robotic surgical system according to item 5, further comprising:

a second display to display the image captured by the endoscope; wherein the second display is arranged independently of the patient-side apparatus and the operator-side apparatus.

(Item 7)

The robotic surgical system according to any one of items 1 to 6, wherein the surgical instrument includes an endoscope;

the operator-side apparatus further includes a first display to display an image captured by the endoscope; and the function to be set to the customized switch includes a function of switching between displaying the image captured by the endoscope in full-screen on the first display and displaying the image captured by the endoscope and an image input from an outside side by side on the first display.

(Item 8)

The robotic surgical system according to item 7, further comprising:

a controller configured or programmed to generate a graphical user interface, superimpose the graphical user interface on the image captured by the endoscope, and display the graphical user interface and the image captured by the endoscope on the first display; wherein the image input from the outside includes an image input from an external device connected to the controller.

(Item 9)

The robotic surgical system according to item 7 or 8, wherein the function to be set to the customized switch includes a function of switching between displaying the image captured by the endoscope in full-screen on the first display, displaying the image captured by the endoscope and the image input from the outside side by side in a lateral direction on the first display, and displaying the image captured by the endoscope and the image input from the outside side by side in a longitudinal direction on the first display.

(Item 10)

The robotic surgical system according to any one of items 1 to 9, wherein the surgical instrument includes an endoscope;

the robotic surgical system further comprises:

a first display to display an image captured by the endoscope; and a controller configured or programmed to generate a graphical user interface, superimpose the graphical user interface on the image captured by the endoscope, and display the graphical user interface and the image captured by the endoscope on the first display; and the function to be set to the customized switch includes a function of displaying, on the first display, the graphical user interface including a first area to display a first graphical display indicating a movable range of the robot arm and an operable range in the movable range of the robot arm, in which the robot arm is operable by the operation unit.

(Item 11)

The robotic surgical system according to item 10, wherein the function to be set to the customized switch includes a function of displaying, on the first display, the graphical user interface including a second area different from the first area to display a second graphical display indicating an operation on the operation unit required to return the operation unit to within the operable range and/or to return the robot arm to within the movable range.

(Item 12)

The robotic surgical system according to any one of items 1 to 11, wherein the surgical instrument includes an endoscope;

the robot arm is an endoscope robot arm to which the endoscope is attached;

the patient-side apparatus further includes:

a first display to display an image captured by the endoscope;

a first surgical instrument robot arm to which a first surgical instrument other than the endoscope is attached; and a second surgical instrument robot arm to which a second surgical instrument other than the endoscope is attached;

the robotic surgical system further comprises a controller configured or programmed to generate a graphical user interface, superimpose the graphical user interface on the image captured by the endoscope, and display the graphical user interface and the image captured by the endoscope on the first display; and the function to be set to the customized switch includes a function of displaying, on the graphical user interface, a mark indicating at least one of the first surgical instrument or the second surgical instrument located outside a field of view of the endoscope when at least one of the first surgical instrument or the second surgical instrument is located outside the field of view.

(Item 13)

The robotic surgical system according to any one of items 1 to 12, wherein the surgical instrument includes an endoscope;

the robotic surgical system further comprises a first display to display an image captured by the endoscope; and the function to be set to the customized switch includes a function of switching the image displayed on the first display between a fluorescence image and a normal image that is not the fluorescence image.

(Item 14)

The robotic surgical system according to any one of items 1 to 13, wherein the surgical instrument includes an endoscope;

the robotic surgical system further comprises a first display to display an image captured by the endoscope; and the function to be set to the customized switch includes a function of digitally zooming the image captured by the endoscope.

(Item 15)

The robotic surgical system according to item 14, wherein a digital zoom factor is changed each time the customized switch is operated by the operator.

(Item 16)

The robotic surgical system according to any one of items 1 to 15, wherein the function to be set to the customized switch includes a function of resetting an error when the error occurs in the robotic surgical system.

(Item 17)

The robotic surgical system according to any one of items 1 to 16, wherein the function to be set to the customized switch includes a function of stopping an alarm sound emitted when an error occurs in the robotic surgical system.

(Item 18)

The robotic surgical system according to any one of items 1 to 17, wherein the operation unit includes:

a support member arranged at a proximal end of the operation unit; and a lever member attached to the support member so as to rotate with respect to the support member; and the customized switch is attached to the lever member.

(Item 19)

The robotic surgical system according to item 18, further comprising:

a housing arranged on the lever member and in which the customized switch is arranged; wherein the housing functions as a finger rest on which fingers of the operator are placed.

(Item 20)

An operator-side apparatus operable to move a robot arm having a tip end to which a surgical instrument is attached, the operator-side apparatus comprising:

an operation manipulator including an operation unit to receive an operation for the surgical instrument; wherein the operation unit includes a customized switch in which a function to be performed by the customized switch is customized by function setting by an operator.

DESCRIPTION OF REFERENCE NUMERALS

1: medical manipulator (patient-side apparatus)
2: remote control apparatus (operator-side apparatus)
4: surgical instrument (first surgical instrument, second surgical instrument)
4b: endoscope
8: controller
8b: display (second display)
8e: external device
21: operation manipulator
21b: operation unit
21ba: support member
23: touch panel (function setting display)
24: monitor (first display)
32: storage
60: manipulator arm (robot arm)
60a, 60b, 60d: manipulator arm (first surgical instrument robot arm, second surgical instrument robot arm)
60c: manipulator arm (endoscope robot arm)
100: surgical system (robotic surgical system)
321bb: first lever member (lever member)
321bh: third switch (customized switch)
321bi: switch housing (housing)
500: setting screen
G: graphical user interface
G8: first area
G9: second area
GR1: first graphical display
GR2: second graphical display
GR21: image captured by endoscope
GR22: image input from the outside
MK1: mark
PP: pivot position

The invention claimed is:

1. A robotic surgical system comprising:

a patient-side apparatus including at least one robot arm having a tip end to which a surgical instrument is attached; and an operator-side apparatus including an operation manipulator comprising a first handle including an operation unit to receive an operation for the surgical instrument, the operation manipulator being operable to move the robot arm; wherein the operation unit includes:

a support member arranged at a proximal end of the operation unit;

a lever member attached to the support member so as to rotate with respect to the support member; and a customized switch attached to the lever member and in which a function to be performed by the customized switch is configured to be customized by a function setting operation.

2. The robotic surgical system according to claim 1, wherein the operator-side apparatus further includes a function setting display to display a setting screen, the setting screen displayed to facilitate the function setting operation to the customized switch.

3. The robotic surgical system according to claim 1, further comprising:

a controller; and a storage to store a set function; wherein the controller is configured or programmed to perform operations comprising:

reading a last set function from the storage; and setting the read last set function to the customized switch when the robotic surgical system is powered on.

4. The robotic surgical system according to claim 2, wherein the setting screen further comprises a plurality of predetermined functions; and a function selected from among the plurality of predetermined functions is set to the customized switch.

5. The robotic surgical system according to claim 1, wherein the surgical instrument includes an endoscope;

the robotic surgical system further comprises a first display to display an image captured by the endoscope; and the function to be set to the customized switch includes at least one of a function of switching the image displayed on the first display between a fluorescence image and a normal image that is not the fluorescence image, or a function of digitally zooming the image captured by the endoscope.

6. The robotic surgical system according to claim 5, further comprising:

a second display to display the image captured by the endoscope; wherein the second display is arranged independently of the patient-side apparatus and the operator-side apparatus.

7. The robotic surgical system according to claim 5, further comprising:

a controller configured or programmed to generate a graphical user interface, superimpose the graphical user interface on the image captured by the endoscope, and display the graphical user interface and the image captured by the endoscope on the first display.

8. The robotic surgical system according to claim 1, wherein the operation unit includes a housing arranged on the lever member and in which the customized switch is arranged; and the housing functions as a finger rest capable of supporting fingers of an operator.

9. The robotic surgical system according to claim 1, wherein the at least one robot arm is a plurality of the robot arms;

each of the plurality of surgical instruments of the robot arms includes an endoscope;

the operator-side apparatus further includes a first display to display an image captured by the endoscope; and the function to be set to the customized switch includes a function of displaying, on the first display, a distance between pivot positions that serve as fulcrums for movement of the surgical instruments attached to the plurality of robot arms.

10. The robotic surgical system according to claim 1, wherein the at least one robot arm is a plurality of the robot arms;

the operator-side apparatus further includes a second operation manipulator comprising a second handle including a second operation unit; and the second operation unit includes:

a second support member arranged at a proximal end of the second operation unit;

a second lever member attached to the second support member so as to rotate with respect to the second support member; and a second customized switch attached to the second lever member and in which a function to be performed by the second customized switch is customized by the function setting.

11. The robotic surgical system according to claim 10, wherein the operator-side apparatus further includes a function setting display to display a setting screen, the setting screen to facilitate the setting of the function to each of the first and second customized switches.

12. The robotic surgical system according to claim 11, wherein the setting screen comprises a first display field in which a plurality of predetermined functions are displayed and a second display field in which a plurality of predetermined functions are displayed; and the function setting display comprises a touch screen configured to:

receive a first selection of a function selected from among the plurality of predetermined functions in the first display field to be set to the first customized switch, and receive a second selection of a function selected from among the plurality of predetermined functions in the second display field to be set to the second customized switch.

13. The robotic surgical system according to claim 10, further comprising:

a controller; and a storage to store a set function; wherein;

the controller is configured or programmed to perform operations comprising:

reading a function last set to each of the first and second customized switches from the storage; and setting the function last set to each of the first and second customized switches when the robotic surgical system is powered on.

14. The robotic surgical system according to claim 10, wherein each of the plurality of surgical instruments of the robot arms includes an endoscope;

the robotic surgical system further comprises a first display to display an image captured by the respective endoscopes; and the function to be set to each of the first and second customized switches includes at least one of a function of switching the image displayed on the first display between a fluorescence image and a normal image that is not the fluorescence image, or a function of digitally zooming the image captured by the respective endoscopes.

15. The robotic surgical system according to claim 10, wherein the second operation unit includes a second housing arranged on the second lever member and in which the second customized switch is arranged; and the second housing functions as a finger rest capable of supporting fingers of an operator.

16. A robotic surgical system comprising:

a patient-side apparatus including an endoscope robot arm to which an endoscope is attached, a first surgical instrument robot arm to which a first surgical instrument other than the endoscope is attached, and a second surgical instrument robot arm to which a second surgical instrument other than the endoscope is attached;

an operator-side apparatus including a first operation manipulator comprising a first handle including a first operation unit to receive an operation for the first surgical instrument, the first operation manipulator being operable to move the first surgical instrument robot arm, and a second operation manipulator comprising a second handle including a second operation unit to receive an operation for the second surgical instrument, the second operation manipulator being operable to move the second surgical instrument robot arm; and a display to display an image captured by the endoscope; wherein the first operation unit includes:

a first support member arranged at a proximal end of the first operation unit;

a first lever member attached to the first support member so as to rotate with respect to the first support member; and a first customized switch attached to the first lever member and in which a function to be performed by the first customized switch is configured to be customized by a function setting operation; and the second operation unit includes:

a second support member arranged at a proximal end of the second operation unit;

a second lever member attached to the second support member so as to rotate with respect to the second support member; and a second customized switch attached to the second lever member and in which a function to be performed by the second customized switch is configured to be customized by the function setting operation.

17. The robotic surgical system according to claim 16, wherein the operator-side apparatus further includes a function setting display to display a setting screen;

the setting screen comprises a first display field in which a plurality of predetermined functions are displayed and a second display field in which a plurality of predetermined functions are displayed are displayed; and the function setting display comprises a touch screen configured to:

receive a first selection of a function selected from among the plurality of predetermined functions in the first display field to be set to the first customized switch, and receive a second selection of a function selected from among the plurality of predetermined functions in the second display field to be set to the second customized switch.

18. The robotic surgical system according to claim 16, further comprising:

a controller; and a storage to store a set function; wherein;

the controller is configured or programmed to perform operations comprising:

reading a function last set to each of the first and second customized switches from the storage; and setting the function last set to each of the first and second customized switches when the robotic surgical system is powered on.

19. A robotic surgical system comprising:

a patient-side apparatus including a robot arm having a tip end to which a surgical instrument including an endoscope is attached;

an operator-side apparatus including an operation manipulator comprising a first handle including an operation unit to receive an operation for the surgical instrument, the operation manipulator being operable to move the robot arm; and a display to display an image captured by the endoscope; wherein the operation unit includes:

a support member arranged at a proximal end of the operation unit;

a lever member attached to the support member so as to rotate with respect to the support member; and a customized switch attached to the lever member and in which a function to be performed by the customized switch is configured to be customized by a function setting operation; and the function to be set to the customized switch includes at least one of a function of switching the image displayed on the display between a fluorescence image and a normal image that is not the fluorescence image, or a function of digitally zooming the image captured by the endoscope.

20. The robotic surgical system according to claim 19, wherein a digital zoom factor of the display of the image captured by the endoscope is changed each time the customized switch is operated when the function set to the customized switch is a digital zooming function.

* * * * *